United States Patent [19]
Gately et al.

[11] Patent Number: 5,853,721
[45] Date of Patent: Dec. 29, 1998

[54] ANTIBODY TO INTERLEUKIN-12 RECEPTOR

[75] Inventors: Maurice Kent Gately, Pine Brook; David Howard Presky, Glen Ridge; Chang-you Wu, Belleville, all of N.J.

[73] Assignee: Hoffmann-La Roche Inc., Nutley, N.J.

[21] Appl. No.: 381,059

[22] Filed: Jan. 31, 1995

[51] Int. Cl.$^6$ .......................... A61K 39/395; C07K 16/00
[52] U.S. Cl. .................... 424/144.1; 424/130.1; 424/134.1; 424/143.1; 435/172.2; 435/343.1; 435/343.2; 530/388.22; 530/388.75
[58] Field of Search ............... 424/130.1, 144.1, 424/143.1, 134.1; 530/387, 388.22, 388.75; 435/240.27, 172.2, 343.1, 2

[56] References Cited

U.S. PATENT DOCUMENTS

| | | | |
|---|---|---|---|
| 5,091,513 | 2/1992 | Huston et al. | 530/387 |
| 5,223,426 | 6/1993 | Skibbens | 435/240.27 |
| 5,536,657 | 7/1996 | Chua et al. | |

FOREIGN PATENT DOCUMENTS

| | | |
|---|---|---|
| 239 400 | 9/1987 | European Pat. Off. |
| 92/11018 | 7/1992 | WIPO |

OTHER PUBLICATIONS

Chan, et al., *J. Exp. Med.*, 173:869–879 (Apr., 1991).
Chizzonite, R., et al., *J. Immunol.*, 147:1548–1556 (Sep. 1, 1991).
Chizzonite, R., et al., *J. Immunol.*, 148:3117–3124 (May 15, 1992).
Chua, A., et al., *J. Immunol.*, 153:128–136 (Jul. 1, 1994).
Desai, et al., *J. Immunol.*, 148:3125–3132 (May 15, 1992).
Gately, et al., *Cell Immunol.*, 143:127–142 (Aug., 1992).
Gately, et al., *J. Immunol.*, 147:874–882 (Aug. 1, 1991).
Huston, et al., *Proc. Natl. Acad. Sci. USA*, 85:5879–5883 (Aug., 1988).
Chua, Anne Expression Cloning of Human IL–12 Receptor Component to gp 130 Apr. 6, 1994 Journal of Immuno. pp. 128–136.
Leonard, JP et al. Prevention of Experimental Autoimmune Encephalomyelitis by AB Against IL–12.

*Primary Examiner*—Lila Feisee
*Assistant Examiner*—Lin Sun-Hoffman
*Attorney, Agent, or Firm*—George W. Johnston; Dennis P. Tramaloni; Alan P. Kass

[57] ABSTRACT

The present invention relates to a novel antibody against the IL-12 receptor and a novel combination of anibodies anainst the IL-12 receptor. The novel anti-IL-12 receptor anbody, designated as 2B10, provided in accordance with the present invention binds to the human IL-12 receptor but which is not capable of inhibiting the binding of human IL-12 to the high affinity human IL-12 receptor and is not capable of neutralizing human IL-12 bioactivity by binding to human IL-12 receptor.

1 Claim, 22 Drawing Sheets

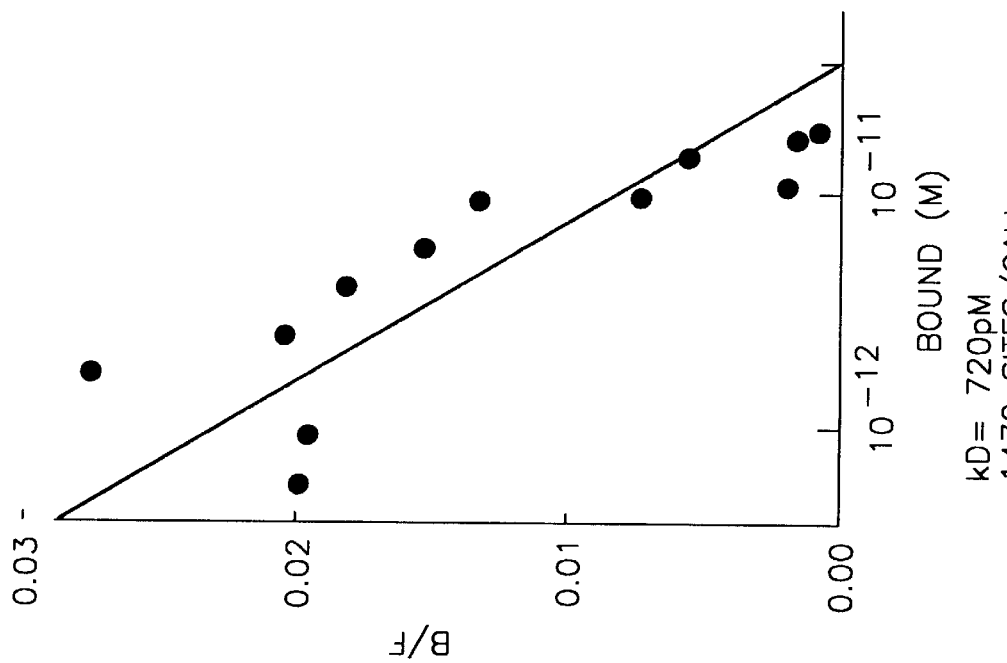
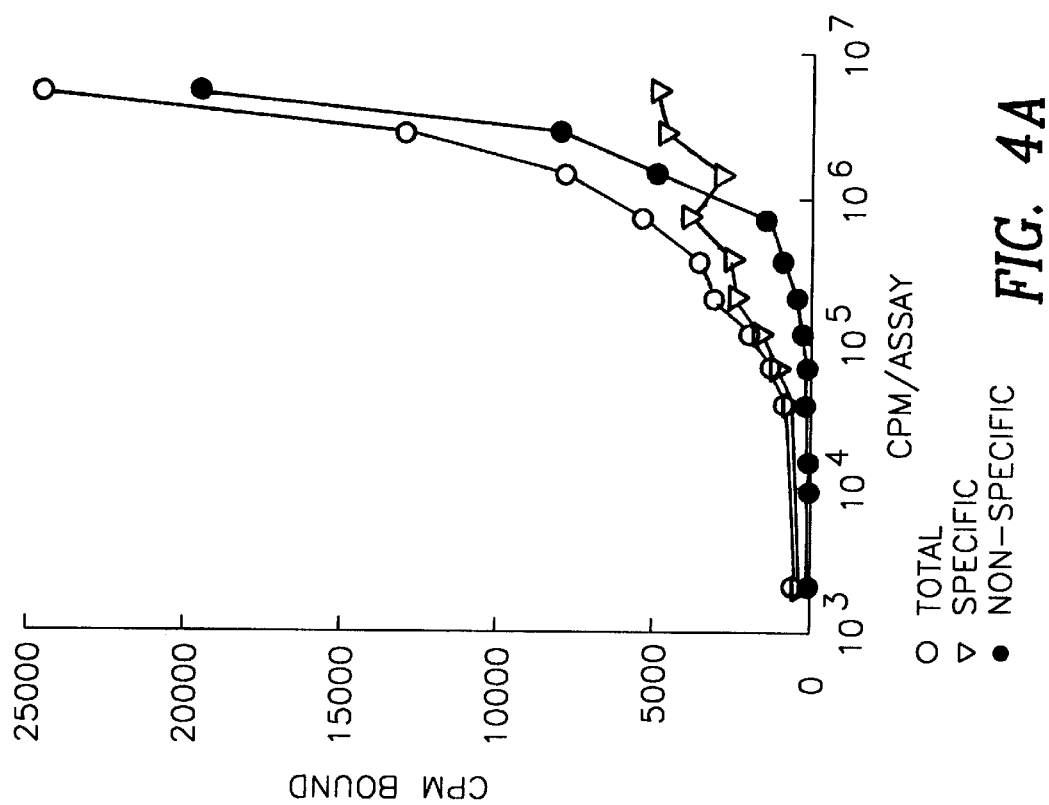
FIG. 4B
FIG. 4A

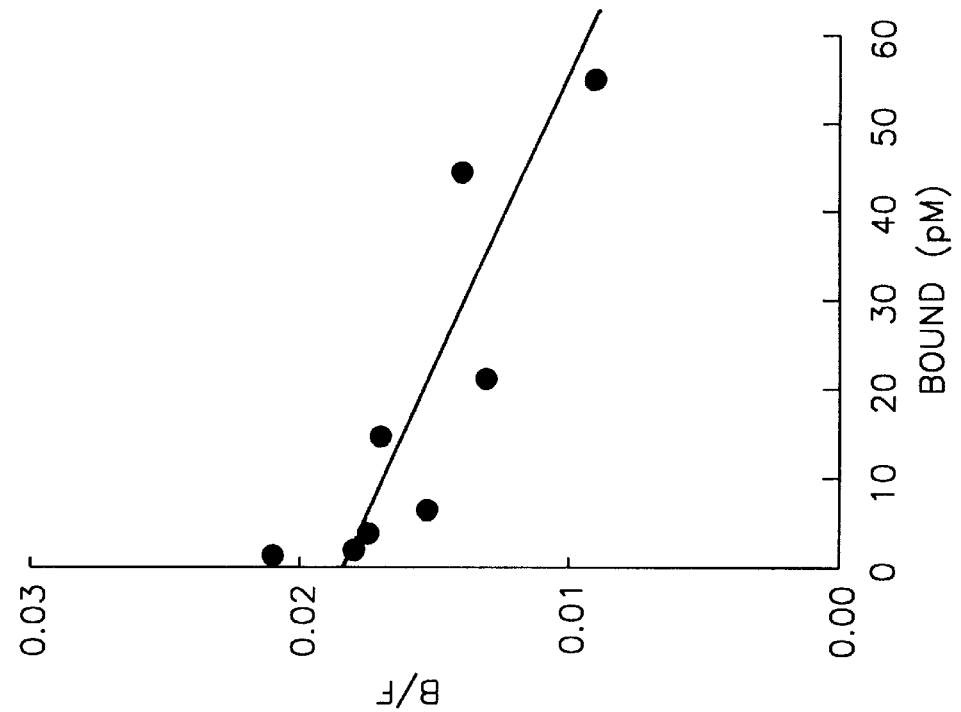
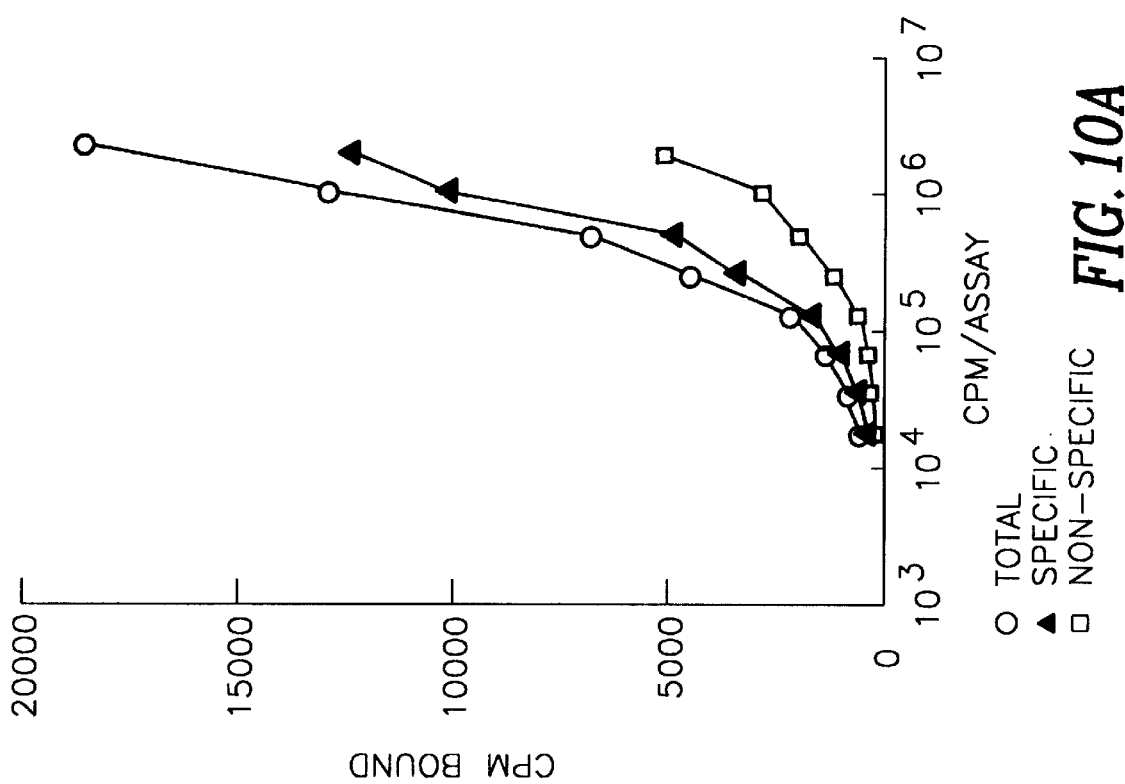
FIG. 10B
FIG. 10A

—□— 2B10
—▼— 2*4E6
--◊-- 2B10 + 2*4E6
--♦-- R+M IgG

ANTIBODY TO INTERLEUKIN-12 RECEPTOR

BACKGROUND OF THE INVENTION

Interleukin-12 (IL-12) is a multifunctional cytokine active on T cells and NK cells. Major activities of IL-12 include its abilities to act as a growth factor for activated T and NK cells, to induce IFN-γ production by both resting and activated T and NK cells, to enhance the lytic activity of NK/LAK cells, and to promote the maturation and activation of Th1 cells, thus facilitating cellular immune responses. IL-12 is a 75-kDa heterodimer composed of disulfide-bonded 40-kDa and 35-kDa subunits. Monoclonal antibodies have been prepared against a partially purified preparation of natural IL-12. These antibodies have been characterized by (1) immunoprecipitation of $^{125}$I-labeled IL-12, (2) immunodepletion of IL-12 bioactivity, (3) Western blotting of IL-12, (4) inhibition of $^{125}$IL-12 binding to its cellular receptor, and (5) neutralization of IL-12 bioactivity. It was determined that antibodies specific for the 40-kDa subunit of IL-12 block receptor binding of $^{125}$IL-12 and neutralize IL-12 bioactivity. See in this regard Chizzonite et al., J. Immunol., 147:1548 (1991).

The initial characterization of the ⁻IL-12 receptor (IL-12R) has been reported for mitogen- and IL-2-activated human peripheral blood mononuclear cells (PBMC) and tonsilar lymphocytes. Radiolabeled IL-12 binding assays demonstrated that at the time of peak expression, mitogen- or IL-2-activated cells expressed 1000 to 9000 IL-12 binding sites/cell with a $K_D$ of approximately 100 to 600 pM. The variations in $K_D$ and sites per cell were dependent on the individual preparations of lymphoblasts. The binding of $^{125}$I-labeled IL-12 to PHA-activated PBMC was saturable and specific, since the binding of radiolabeled ligand was only inhibited by IL-12 and not by other cytokines. Kinetic studies revealed that maximum expression of IL-12R occurred earlier on PHA-activated PBMC as compared with PBMC activated by IL-2, and that expression of IL-12R on these cells correlated with their ability to proliferate in response to IL-12. See Chizzonite et al., J. Immunol., 148:3117 (1992) and Desai et al., J. Immunol., 148:3125 (1992). Activation of T cells or NK cells results in up-regulation of IL-12R expression; on the other hand, B cell activation, at least under some circumstances, appears not to be associated with enhanced expression of IL-12R.

One subunit of the human IL-12R has been cloned and expressed. This subunit has been designated as IL-12R β. See, Chua et al., J. Immunol., 153:128 (1994). As discussed below, the function of the IL-12R β chain in mediating various biologic activities of IL-12 was evaluated. We have shown that two mAbs to IL-12R β, 2B10 and 2*4E6, when used in a combination, strongly blocked IL-12-induced proliferation of PHA-activated human lymphoblasts but had no effects on IL-2-, IL-4-, or IL-7-induced lymphoblast proliferation. In addition, 2B10 and 2*4E6 mAbs in combination markedly inhibited IL-12-mediated LAK cell activation and IL-12-induced IFN-γ production by resting PBMC.

It has been previously shown that PHA-activated human lymphoblasts produced as described above consisted of >90% CD3⁺T cells (Gately et al., J. Immunol., 147:874, 1991). On the other hand, IL-12-induced LAK cell activity was shown to be mediated by NK cells but not T cells (Gately et al., Cell. Immunol., 143: 127, 1992). Finally IL-12-induced IFN-γ secretion by resting PBMC appears to involve both T and NK cells (Chan et al., J. Exp. Med., 173: 869, 1991). Thus the ability of mAbs to IL-12R β to inhibit IL-12-induced lymphoblast proliferation, LAK cell activation, and IFN-γ secretion strongly suggests that the IL-12R β chain is an essential component of the functional IL-12R on both T and NK cells. Moreover, it appears to be an essential part of the IL-12R on resting, as well as activated, lymphocytes.

SUMMARY OF THE INVENTION

The present invention relates to a novel antibody against the IL-12R and a novel combination of antibodies against the IL-12R. The novel anti-IL-12R antibody, designated as 2B10, provided in accordance with the present invention binds to the human IL-12 receptor but which is not capable of inhibiting the binding of human IL-12 to the high affinity human IL-12 receptor and is not capable of neutralizing human IL-12 bioactivity by binding to human IL-12 receptor. With regard to the novel combination of monoclonal antibodies (mAb), it has been found that the combination of 2B10 and 2*4E6 strongly inhibit (a) IL-12 induced proliferation of activated T cells; (b) IL-12 induced secretion of interferon-γ by resting PBMC; and (c) IL-12 mediated LAK cell activation, as discussed below. The suitable monoclonal antibody to IL-12R can be modified by known methods to provide chimeric, humanized or single chain antibody embodiments.

The IL-12R antibody of the present invention can be used to determine IL-12 receptor expression on human cells, such as peripheral blood lymphocytes and bone marrow cells, in normal and pathological conditions. The combination of monoclonal antibodies 2B10 and 2*4E6 can also be used to block IL-12 binding to its receptor and thus block its biologic activity. Neutralizing antibody combination of the present invention can thus be used for therapeutic intervention in a number of disease states in which IL-12 plays an essential role in the pathogenesis, such as septic shock and autoimmune diseases including multiple sclerosis. This invention also relates to a method of ascertaining the immune status of an individual having an immune system abnormality. The method comprises determining the levels of IL-12R preferably by immunochemical means in a biological fluid of the individual and relating the values obtained to predetermined values as indicative of an abnormal condition or of a change in immune status. The information can be used in the monitoring and treatment of individuals undergoing immunosuppressive therapy for diseases such as rheumatoid arthritis.

BRIEF DESCRIPTION OF THE FIGURES

FIGS. 4A and 4B—Equilibrium binding of $^{125}$I-2*4E6 to PHA-activated PBMC at Room Temperature FIG. 4A: Lymphoblasts (1×10$^6$ cells) were incubated for 2 hrs at room temperature with increasing concentrations of $^{125}$I-2*4E6 in the absence (○) or presence (•) of 25 nM unlabeled 2*4E6. Total (○) and non-specific (•) cell bound radioactivity were determined as discussed below. Specific binding of $^{125}$I-2*4E6 (▼) was calculated by subtracting non-specific binding from total binding. FIG. 4B shows analysis of the binding data according to the method of Scatchard as determined by Ligand computer program with a single-site model.

Figure 5A: Kit 225/K6 cells (1×10$^6$ cells) were incubated for 2 hrs at room temperature with increasing concentrations of $^{125}$I-2*4E6 in the absence (•) or presence (▽) of 25 nM unlabeled 2*4E6. Total (•) and non-specific (▽) cell bound radioactivity were determined as discussed below. Specific binding of $^{125}$I-2*4E6 (▼) was calculated by subtracting nonspecific binding from total binding. FIG. 5B shows analysis of the binding data according to the method of Scatchard as determined by Ligand with a single-site model.

The data are expressed as the amount of $^{125}$I-2*4E6 bound [CPM BOUND (Percent)] to the cells in the presence of the indicated concentrations of unlabeled antibody or IL-12 when compared with the total specific binding in the absence of unlabeled competitor.

Figure 7B:
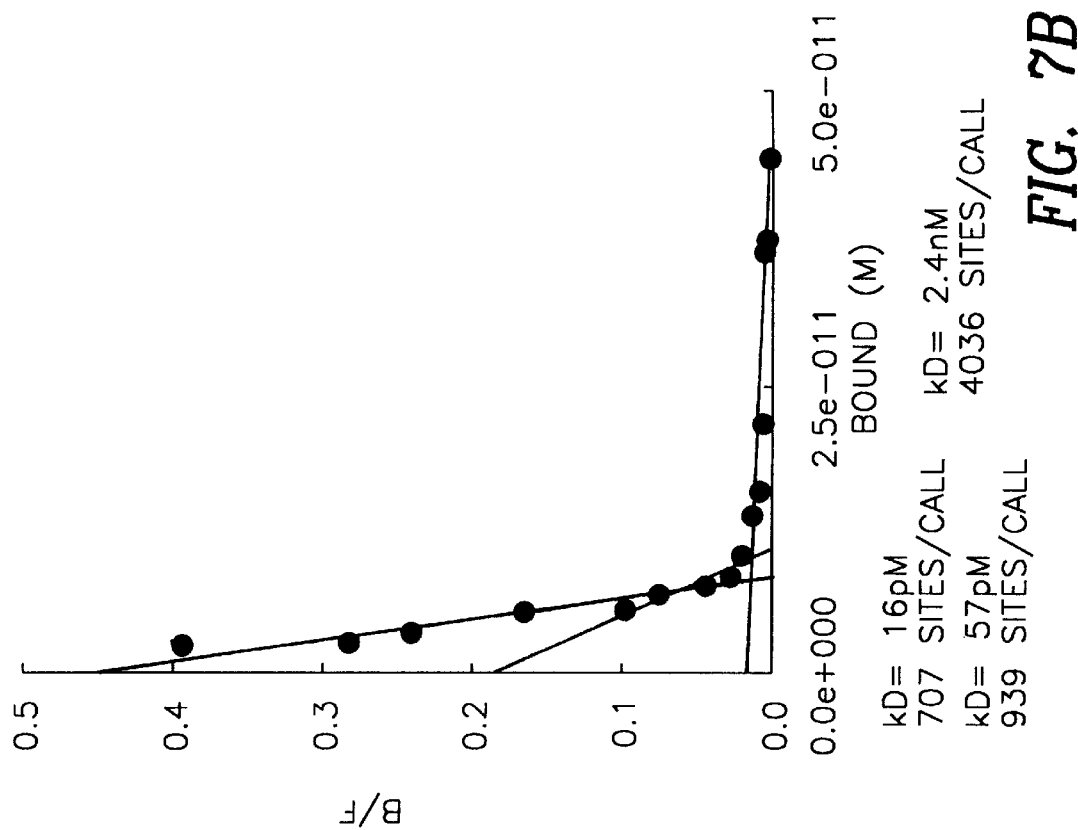
Figure 7A:
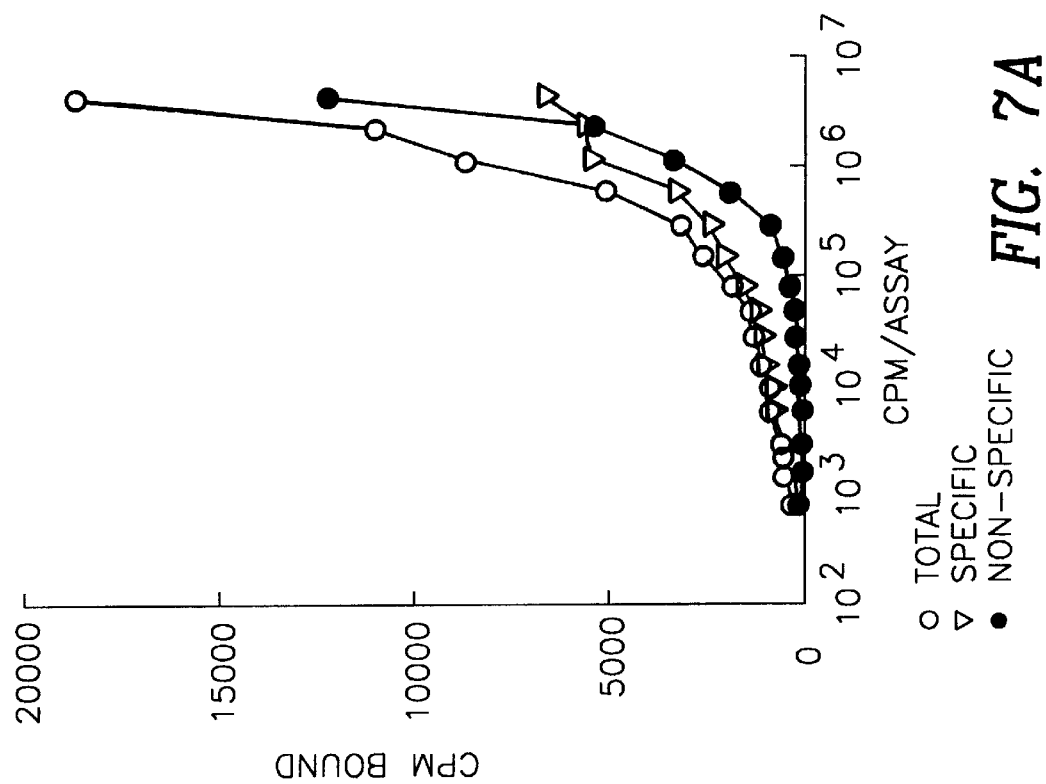

FIGS. 7A and 7B Equilibrium Binding of $^{125}$I-IL-12 to Human Kit 225/K6 Cells at Room Temperature FIG. 7A: Kit 225/K6 cells (1×10$^6$ cells) were incubated for 2 hrs at room temperature with increasing concentrations of $^{125}$I-IL-12 in the absence (○) or presence (•) of 50 nM unlabeled IL-12. Total (○) and non-specific (•) cell bound radioactivity were determined as described in Materials and Methods. Specific binding of $^{125}$I-IL-12 (▼) was calculated by subtracting non-specific binding from total binding. FIG. 7B shows analysis of the binding data according to the method of Scatchard as determined by Ligand with a single-site model.

Figure 8B:
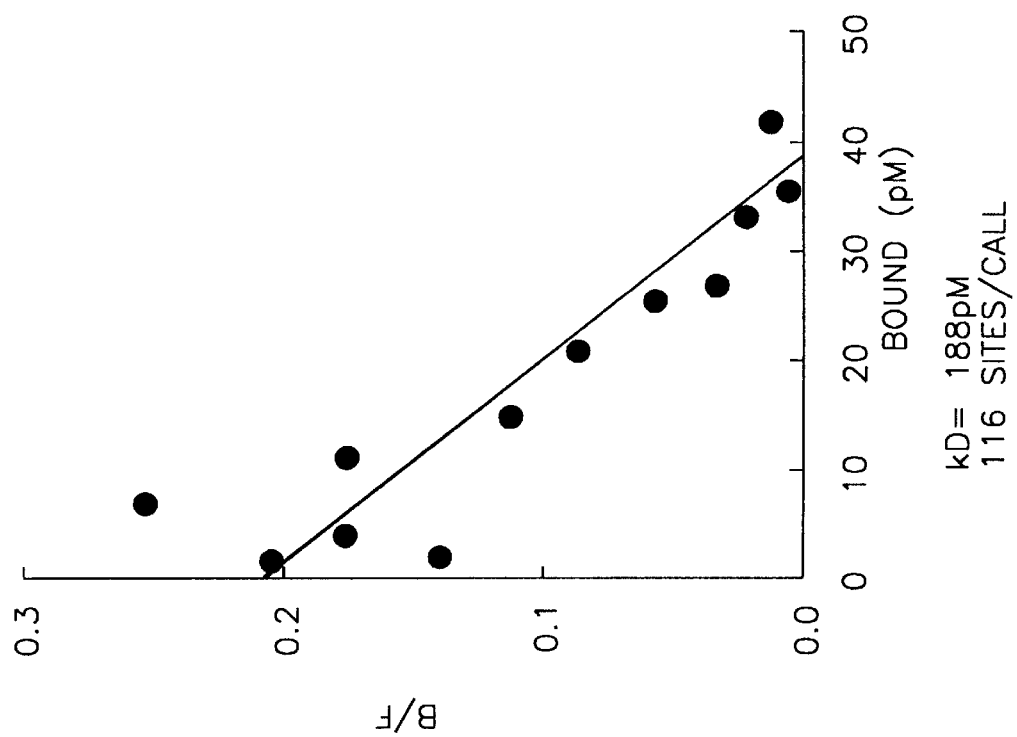
Figure 8A:
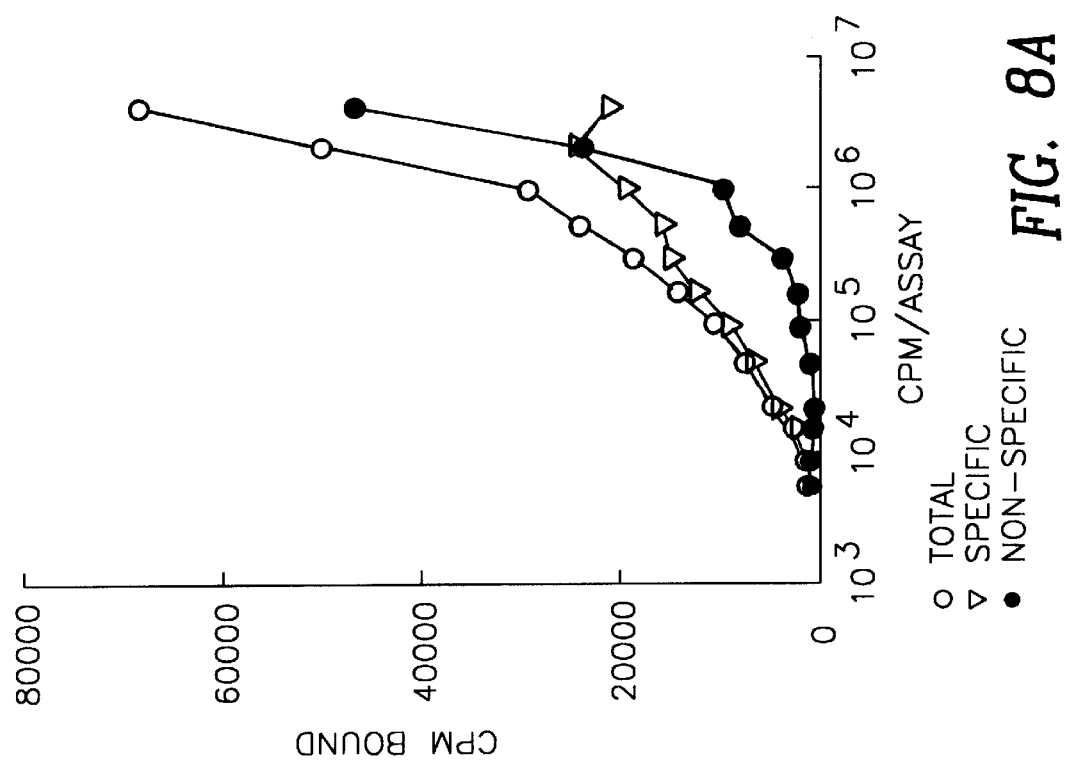

FIGS. 8A and 8B—Equilibrium Binding of $^{125}$I-IL-12 to Detergent Solubilized IL-12R from Kit 225/K6 Cells FIG. 8A: Kit 225/K6 cells (1.5×10$^8$ cells/ml) were solubilized with 8 mM CHAPS extraction buffer and the cell extract (0.2 ml) was immunoprecipitated for 16 hrs at 4° C. with mAb 2*4E6 immobilized on goat anti-mouse IgG coupled to agarose as discussed below. Following this incubation, the beads were pelleted, washed and resuspended in IP buffer containing $^{125}$I-IL-12 at concentrations ranging from 7 pM to 7.5. The IL-12R immobilized on the 2*4E6 coated beads was incubated with $^{125}$I-IL-12 for 2 hrs at RT and IL-12R bound radioactivity was determined in the presence of 50 nM unlabelled IL-12. FIG. 8B shows analysis of the binding data according to the method of Scatchard as determined by Ligand with a single-site model.

Figure 9:
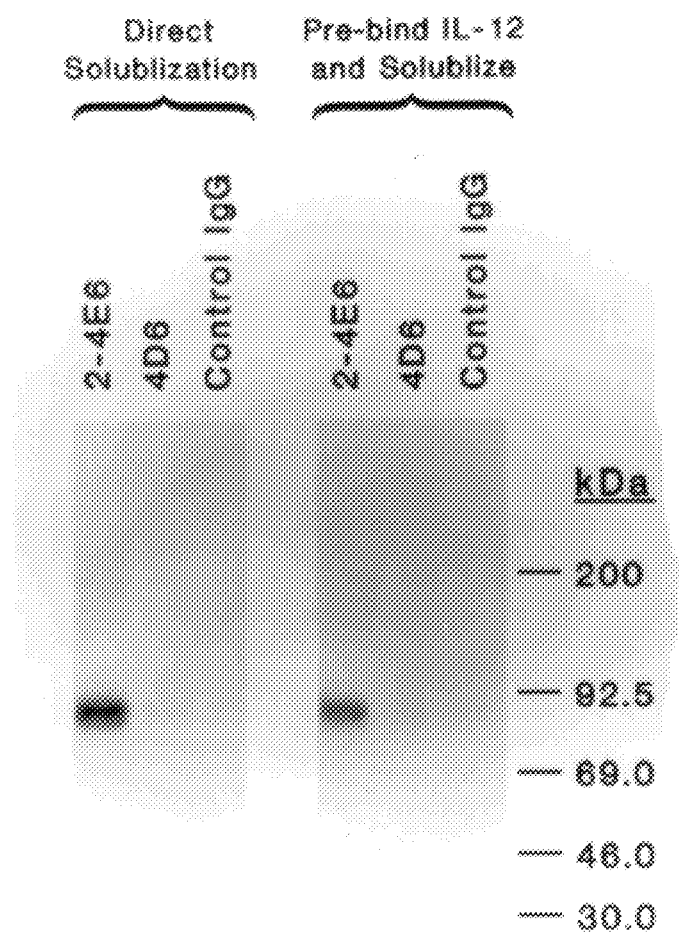

FIG. 9—Western Blot Analysis of Detergent Solubilized IL-12R with mAb 2*4E6

PHA-activated PBMC (1×10$^8$ cells/ml) were solubilized with 8 mM CHAPS extraction buffer, and the cell extract (1 ml) was immunoprecipitated as described in FIG. 8. Following this incubation, the beads were pelleted, washed and the bound proteins released by treatment with 0.1M glycine pH 2.3. The released proteins were separated by non-reducing SDS/PAGE on 8% gels transferred to nitrocellulose membrane and probed with $^{125}$I-2*4E6 as discussed below. The molecular sizes indicated in the margins were estimated from molecular weight standards (Amersham Prestained High Molecular Weight Standards) run in parallel lanes. Exposure time was 7 days.

FIGS. 10A and 10B—Equilibrium Binding of $^{125}$I-IL-12 to Human Recombinant IL-12 Receptor β Subunit Expressed in COS Cells FIG. 10A: COS cells were transfected with a plasmid expressing human rIL-12R β as discussed below. Three days later, transfected cells (1×10$^4$ cells) were incubated for 2 hrs. at room temperature with increasing concentration of $^{125}$I-IL-12 in the absence (○) or presence (□) of 50 nM unlabeled IL-12. Total (○) and non-specific (□) cell bound radioactivity were determined as discussed below. Specific binding of $^{125}$I-IL-12 (▲) was calculated by subtracting non-specific binding from total binding. Figure 10B shows analysis of the binding data according to the method of Scatchard as determined by Ligand with a single-site model.

Figure 11B:
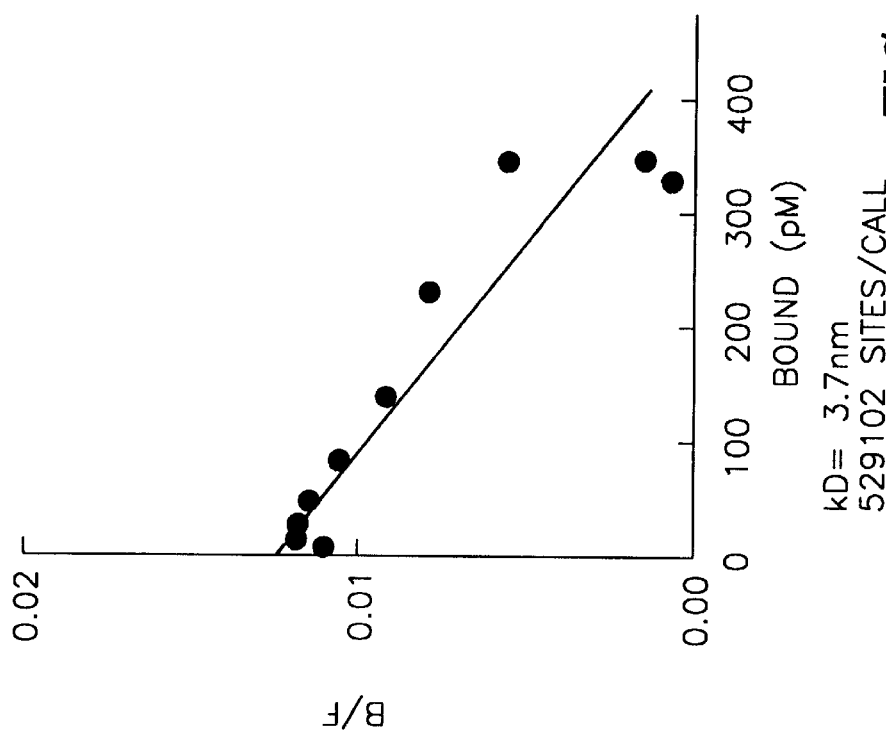
Figure 11A:
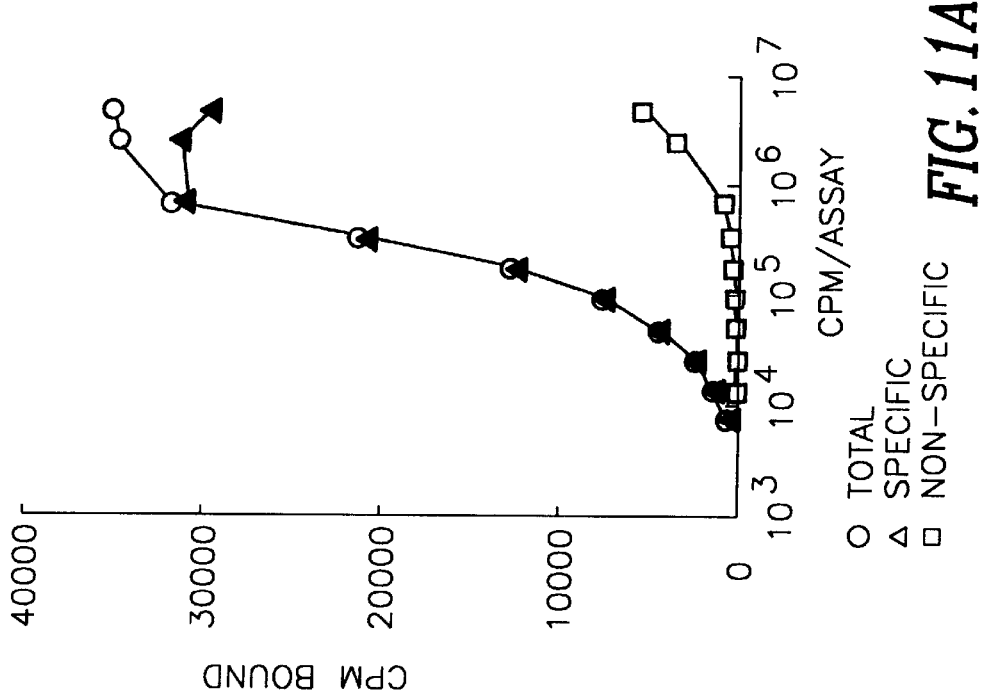

FIGS. 11A and 11B—Equilibrium Binding of $^{125}$I-2*4E6 to Human Recombinant IL-12 Receptor β Subunit Expressed in COS Cells.

FIG. 11A: COS cells were transfected with a plasmid expressing human rIL-12R β as discussed below. Three days later, transfected cells (1×10⁴ cells) were incubated for 2 hrs at room temperature with increasing concentrations of $^{125}$I-2*4E6 in the absence (○) or presence (□) of 50 nM unlabeled 2*4E6. Total (○) and non-specific (□) cell bound radioactivity were determined as discussed below. Specific binding of $^{125}$I-2*4E6 (●) was calculated by subtracting non-specific binding from total binding. FIG. 11B shows analysis of the binding data according to the method of Scatchard as determined by Ligand with a single-site model.

Figure 12A:
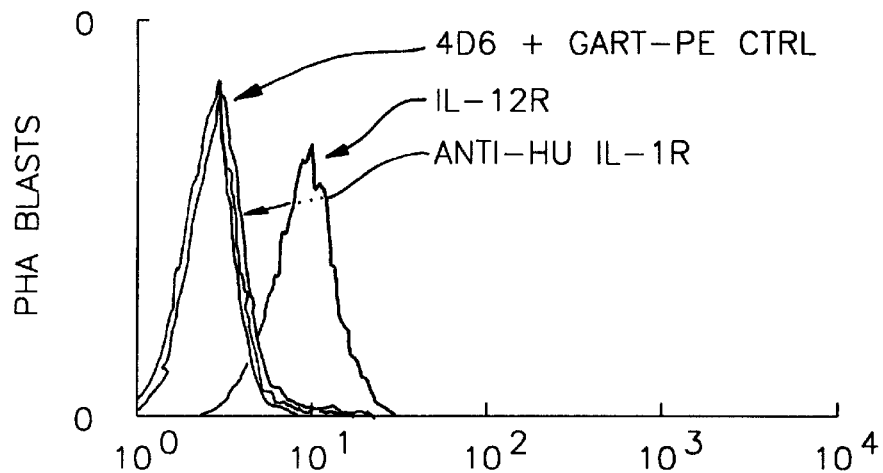
Figure 12B:
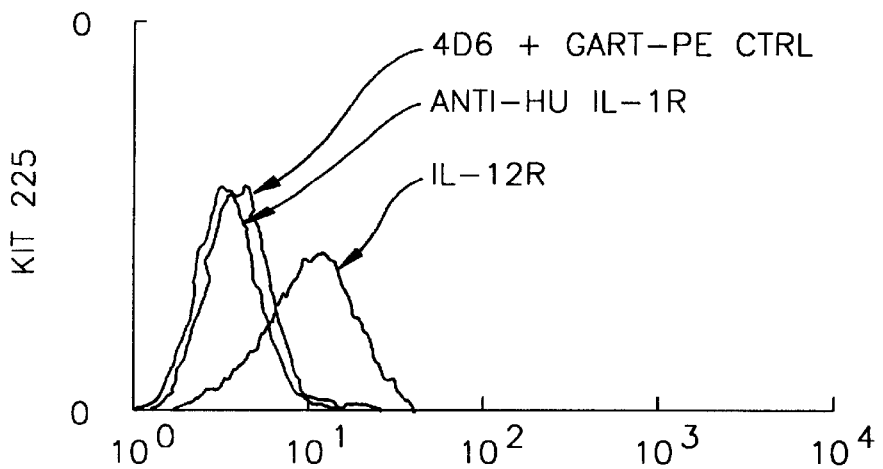
Figure 12C:
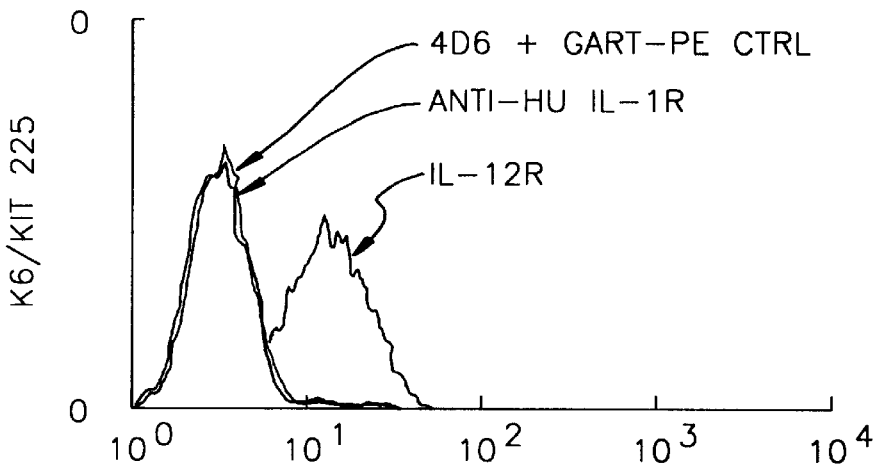

FIGS. 12A, 12B and 12C—Detection of IL-12 Receptor on Human Cells by Flow Cytometry Day 4 PHA-activated lymphoblasts (FIG. 12A), Kit-225 (FIG. 12B) and Kit 225/K6 cells (FIG. 12C) were analyzed for IL-12R expressing cells by the indirect fluorescent antibody-labeling technique discussed below. FIGS. 12A, 12B, and 12C, for the respective cells above, depict specific staining for IL-12R obtained in the presence of mAb 2*4E6 (anti-HuIL-12R β) and non-specific staining obtained in the presence of a control antibody specific for IL-1 receptor (anti-Hu IL-1R), a control antibody specific for human IL-12 (4D6+GART-PE CTRL) and the goat anti-mouse antibody conjugated with PE (GART-PE CTRL).

Figure 13:
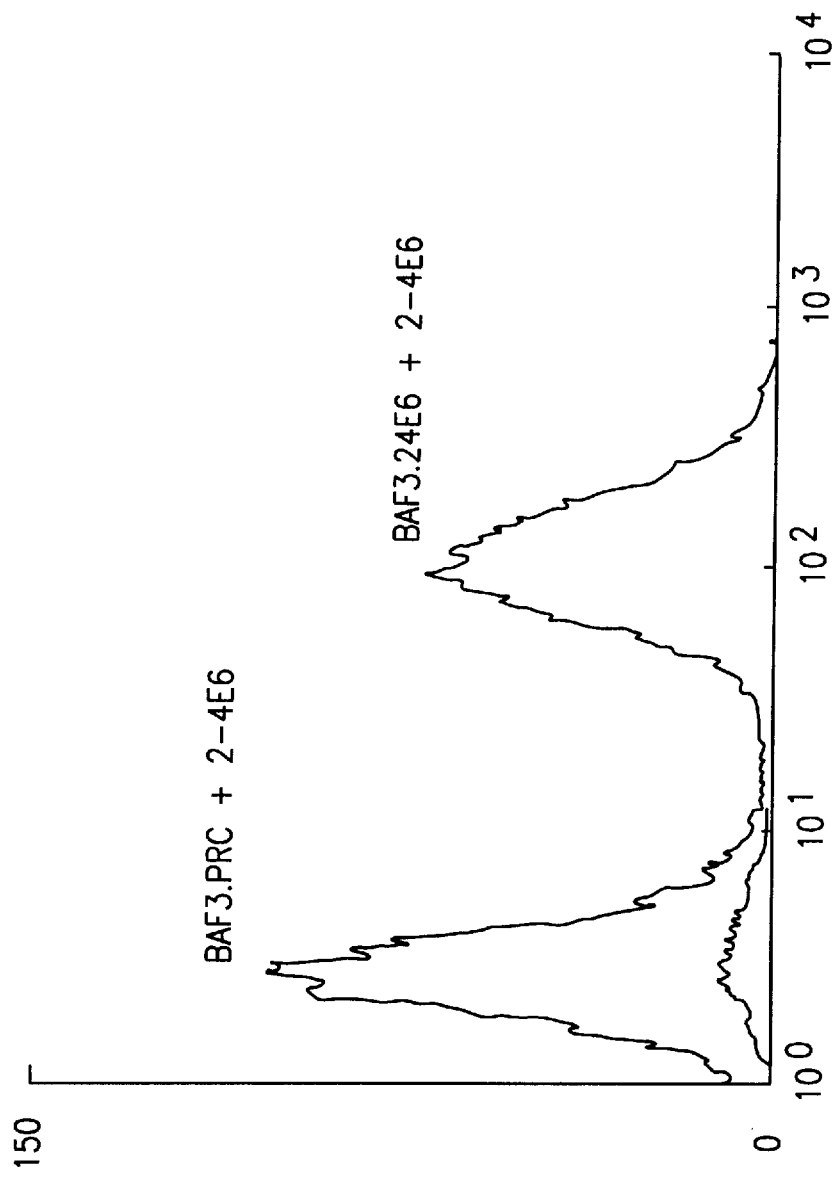

FIG. 13—Flow Cytometric Analysis of mAb 2*4E6 Binding to Transfected BaF3 Cells

BaF3 cells transfected with a pRC-RSV expression construct encoding the IL-12R β (BaF3.24E6) or pRC-RSV without the IL-12R β (BaF3.PRC) were incubated with anti-IL-12R mAb 2*4E6 followed by FITC-conjugated goat anti-mouse IgG, and were analyzed by flow cytometry as discussed below.

Figure 14:
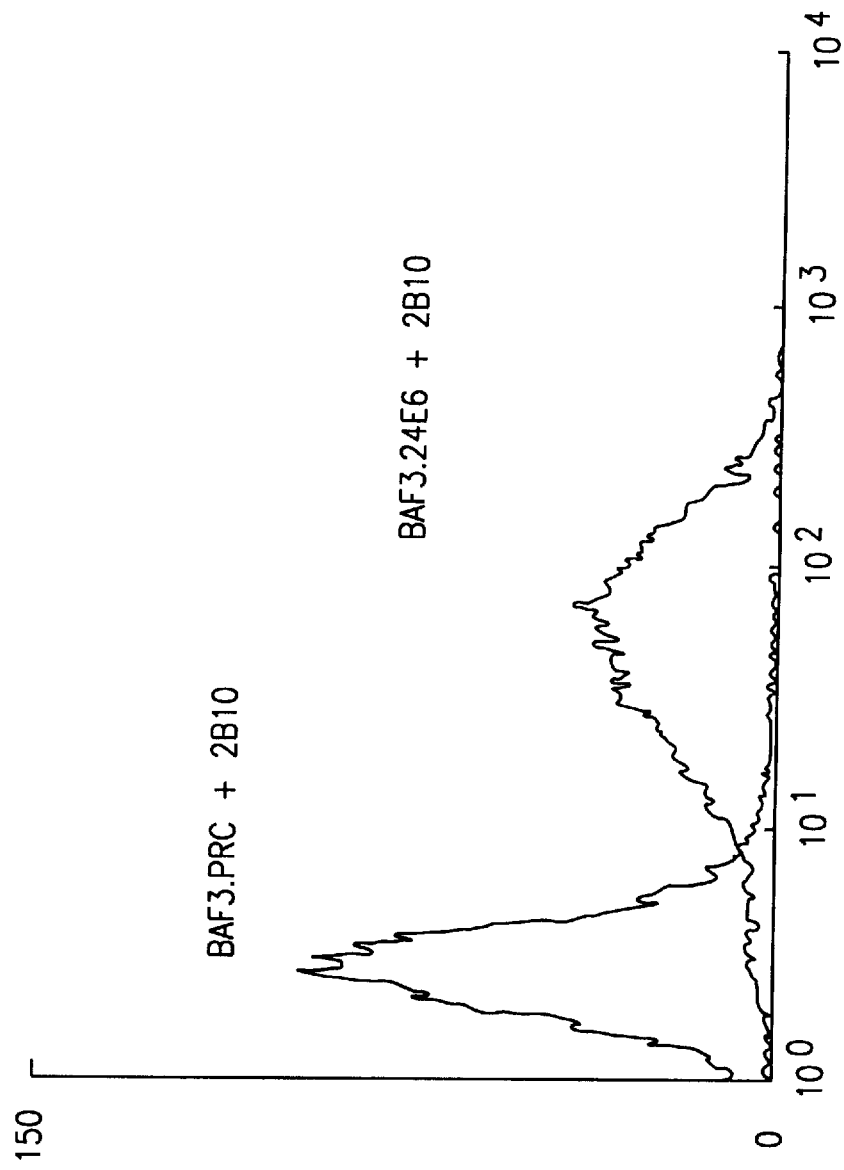

FIG. 14—Flow Cytometric Analysis of mAb 2B10 Binding to Transfected BaF3 Cells

BaF3 cells transfected with a pRC-RSV expression construct encoding the IL-12R (BaF3.24E6) or pRC-RSV without the IL-12R (BaF3.PRC) were incubated with mAb 2B10 followed by FITC-conjugated goat anti-rat IgG, and were analyzed by flow cytometry as discussed below.

Figure 15:
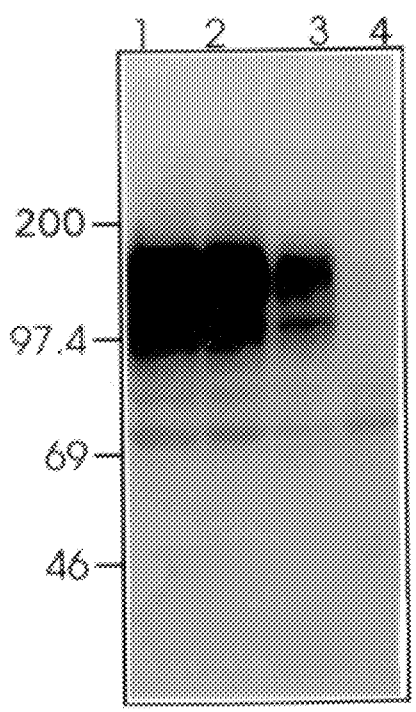

FIG. 15—Western Blot Analysis of BaF3.24E6 Cell Lysates Using Horseradish Peroxidase-Conjugated mAb 2B10

BaF3.PRC (1×10⁶ cells, lane 4) and BaF3.24E6 cells (1.5×10⁶ cells, lane 1; 1×10⁶ cells, lane 2; 0.5×10⁶ cells, lane 3) were solubilized with CHAPS extraction buffer at a cell density of 1×10⁸ cells/ml. The cell lysates were separated by non-reducing SDS/PAGE on a 4–20% gradient gel, the proteins were electrophoretically transferred to nitrocellulose, the membranes were probed with horseradish peroxidase-conjugated 2B10 and developed using ECL Western Blotting Detection Reagent (Amersham, Buckinghamshire, England) as discussed below. The migration of molecular weight standards (Amersham Prestained High Molecular Weight Standards) run in parallel lanes are indicated.

Figure 16:
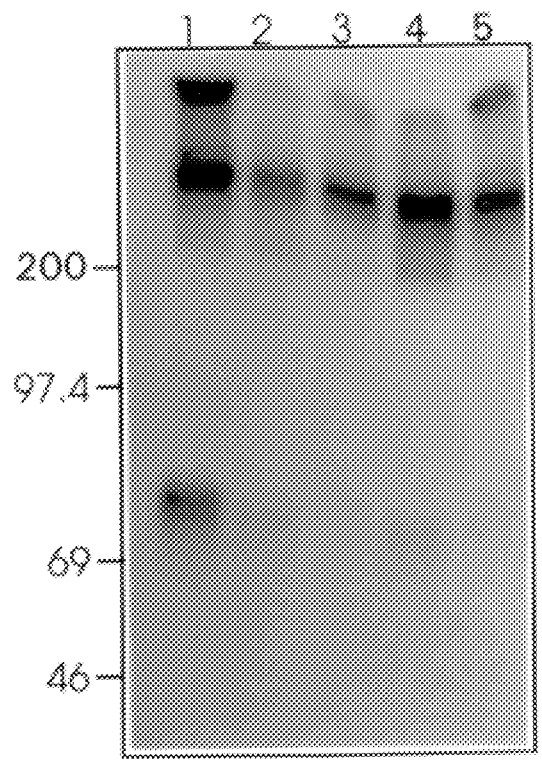

FIG. 16—Immunoprecipitation of Solubilized $^{125}$I-IL-12/IL-12R Crosslinked Complex from PHA-Activated Lymphoblasts by mAb 2B10

Solubilized $^{125}$I-IL-12/IL-12R crosslinked complex was prepared from PHA-activated lymphoblasts and precipitated with 50 μl of wheat germ lectin sepharose beads (Sigma Chemical Co., St. Louis, Mo.; lane 1), 2.5 μg mAb 2B10 (lanes 2 and 3), or 2.5 μg mAb 2*4E6 (lanes 4 and 5) as described below. The precipitated proteins were separated on an 8% SDS/PAGE gel and visualized by autoradiography. The migration of molecular weight standards (Amersham Prestained High Molecular Weight Standards) run in parallel lanes are indicated.

Figure 17:
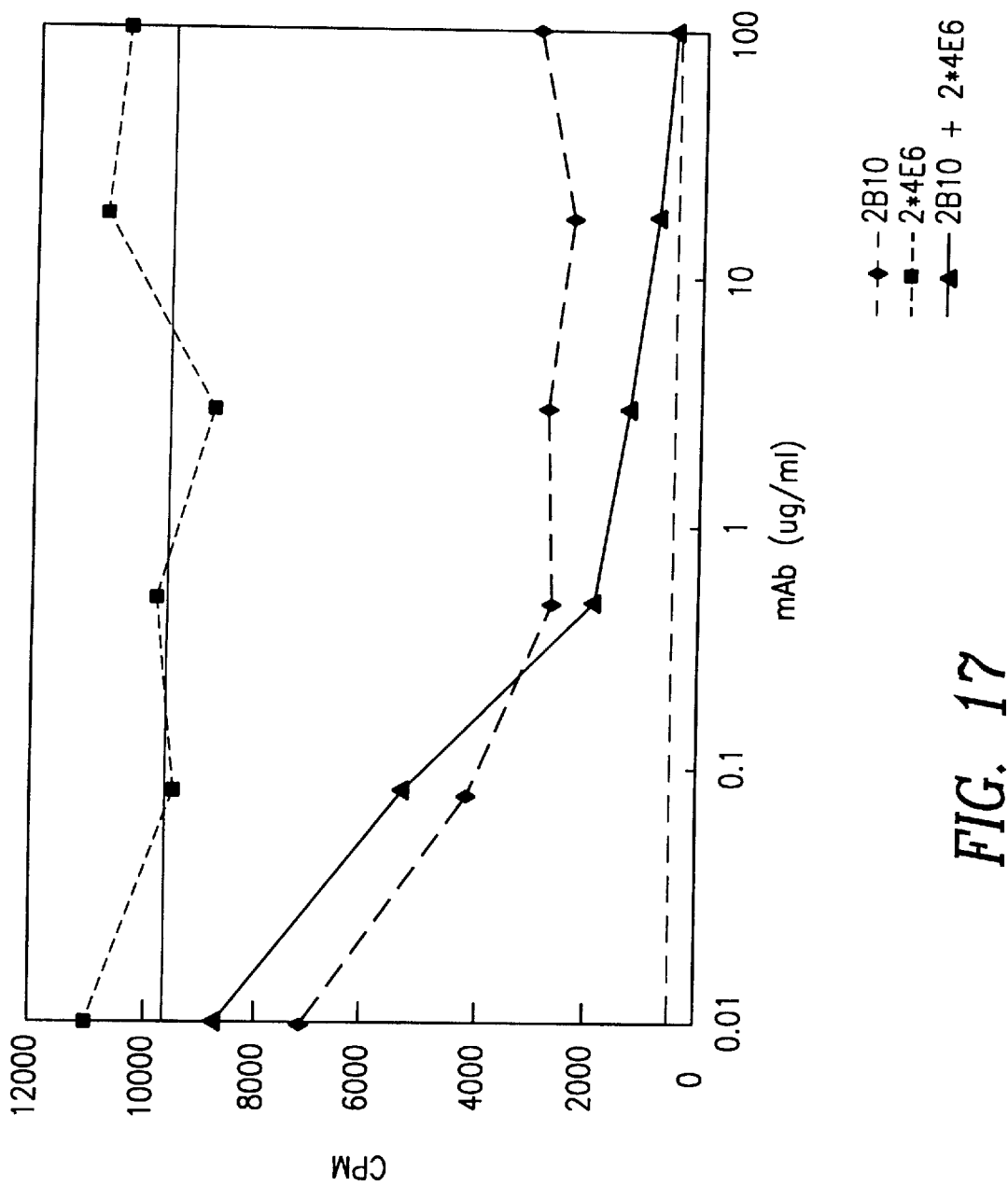

FIG. 17—Inhibition of $^{125}$I-IL-12 Binding to Transfected COS-7 Cells Expressing Recombinant IL-12R β By Anti-IL-12R β mAb 2B10 and 2*4E6

Transfected COS-7 cells (1×10⁵) expressing recombinant IL-12R β, prepared as discussed below, were preincubated with the indicated concentrations of mAb 2B10 (◆), 2*4E6 (•), or a 1:1 mixture of both antibodies (●) for 60 min at room temperature before addition of $^{125}$I-IL-12 (700 pM). $^{125}$I-IL-12 binding was determined as discussed below. Total Binding (solid reference line) was determined in the absence of any unlabelled IL-12 or mAb, and Non-Specific Binding (dashed reference line) was determined in the presence of 133 nM unlabelled IL-12.

Figure 18:
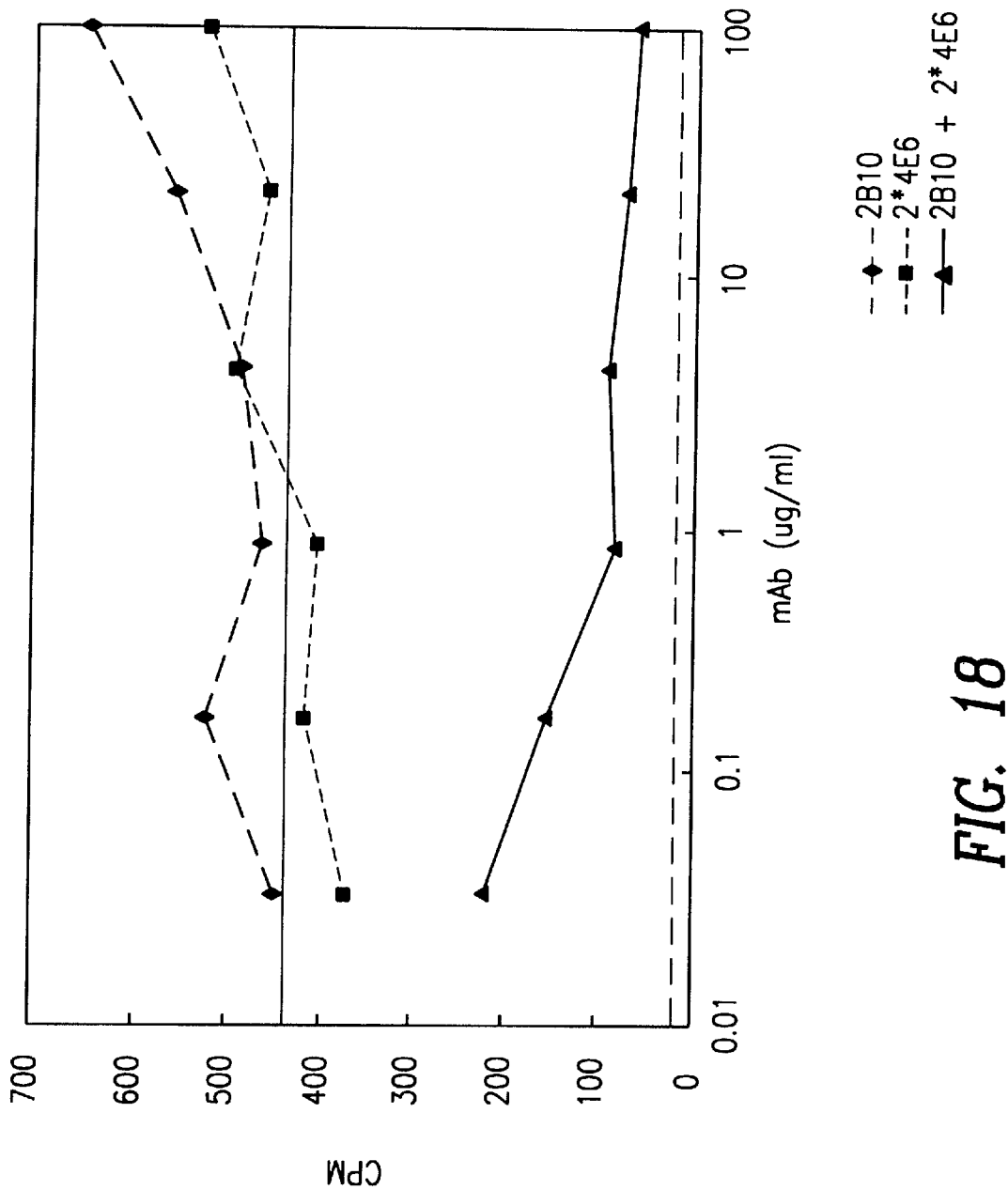

FIG. 18—Inhibition of $^{125}$I-IL-12 Binding to PHA-Activated Lymphoblasts by Anti-IL-12R β mAb 2B10 and 2*4E6

PHA-activated lymphoblasts (7.5×10⁵) were preincubated with the indicated concentrations of mAb 2B10 (◆), 2*4E6 (•), or a 1:1 mixture of both antibodies (●) for 60 min at room temperature before addition of $^{125}$I-IL-12 (50 pM). $^{125}$I-IL-12 binding was determined as discussed below. Total Binding (solid reference line) was determined in the absence of any unlabelled IL-12 or mAb, and Non-Specific Binding (dashed reference line) was determined in the presence of 133 nM unlabelled IL-12.

Figure 19:
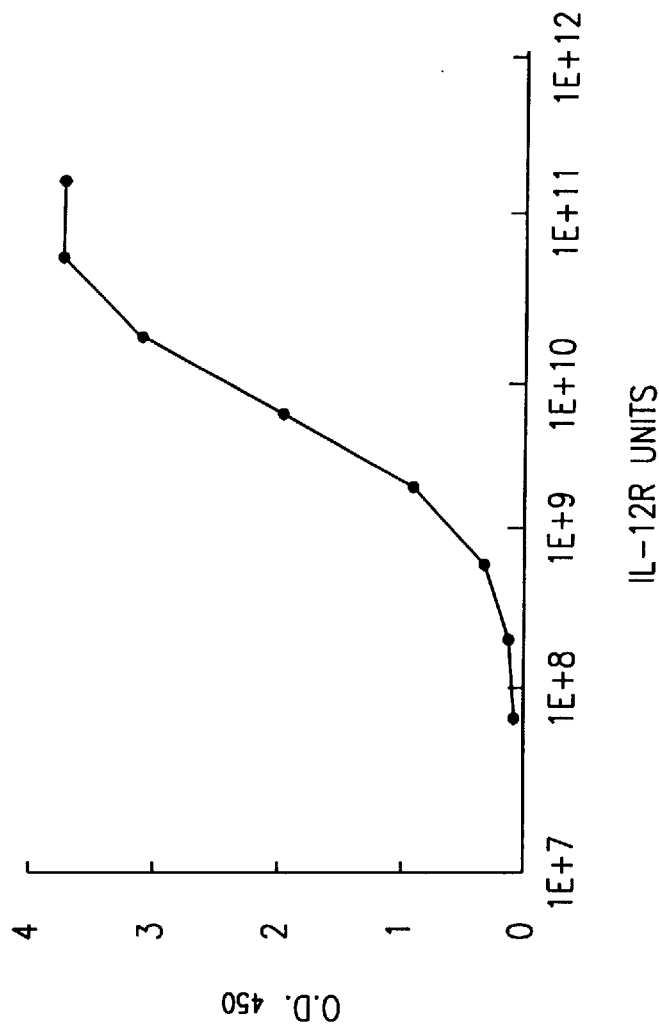
Figure 20A:
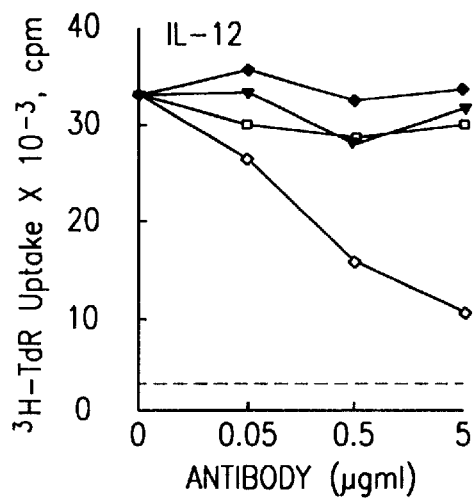
Figure 20B:
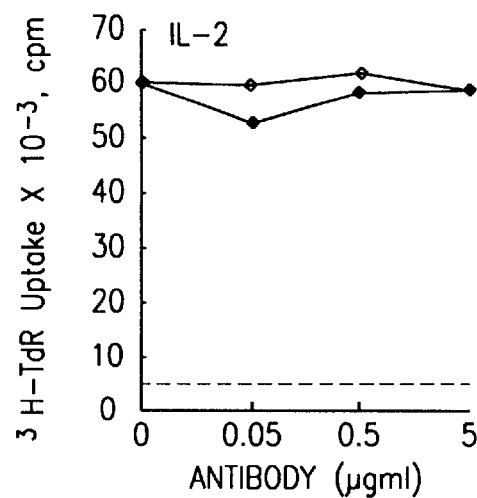
Figure 20C:
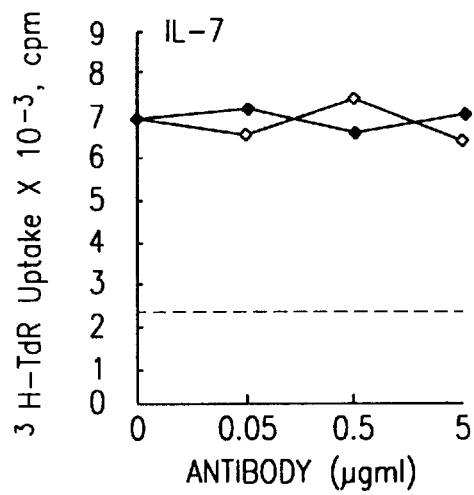
Figure 20D:
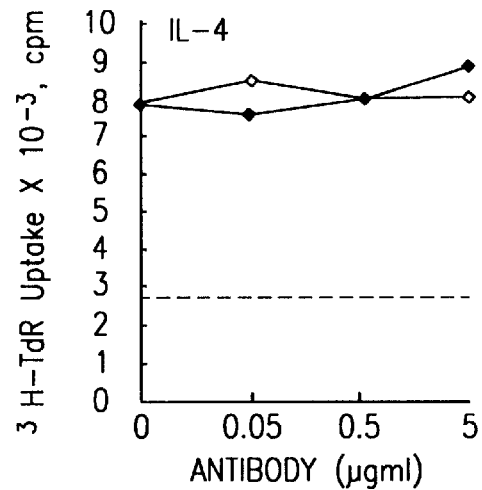

FIG. 19—Representative Standard Curve for Soluble IL-12R β ELISA.

BaF3.24E6 cell lysates were prepared and analyzed in the soluble IL-12R β ELISA as discussed below. Results for a representative standard curve are shown. IL-12R Units were calculated as discussed below.

FIG. 20—Specific Inhibition of IL-12-induced Lymphoblast Proliferation by mAbs to Human IL-12Rβ Chain PHA-activated lymphoblasts were incubated for 48 hrs with IL-12 (200 pg/ml) (Panel A), IL-2 (5 units/ml) (Panel B), IL-7 (500 pg/ml)

(Panel C) or IL-4 (20 units/ml) (Panel D) in the presence or absence of monoclonal 2B10 and/or 2*4E6 anti-human IL-12R β or a 1:1 mix of control rat and mouse IgG (R+M IgG) at the indicated concentrations. When added in combination, 2B10 and 2*4E6 were used as a 1:1 mixture. Lymphoblast proliferation was quantitated by measurement of tritiated thymidine (³H-TdR) incorporation as described below. The horizontal dotted line in each panel indicates the level of ³H-TdR incorporation in cultures without added cytokines. The data are representative of four experiments with similar results.

Figure 21:
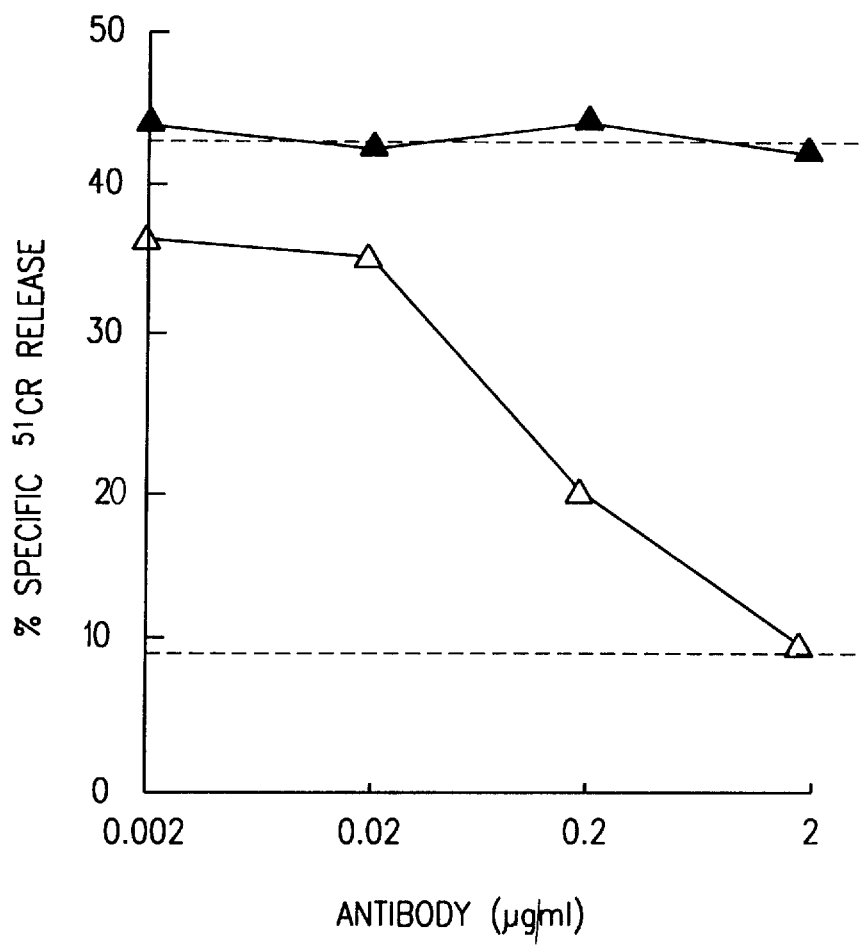

FIG. 21—mAbs to IL-12R β Inhibit IL-12-induced LAK Cell Activation

Freshly isolated PBMC were incubated with IL-12 (500 pg/ml) and the indicated concentration of a 1:1 mixture of 2B10 and 2*4E6 or of control rat and mouse IgG. The cells were harvested 5 days later and assayed for lytic activity against $^{51}$Cr-labeled Daudi target cells. The upper horizontal dotted line indicates the level of lytic activity observed in cultures receiving IL-12 without added IgG and the lower horizontal dotted line the level of spontaneous lytic activity in cultures that did not receive IL-12. Similar results were observed in four additional experiments.

Figure 22:
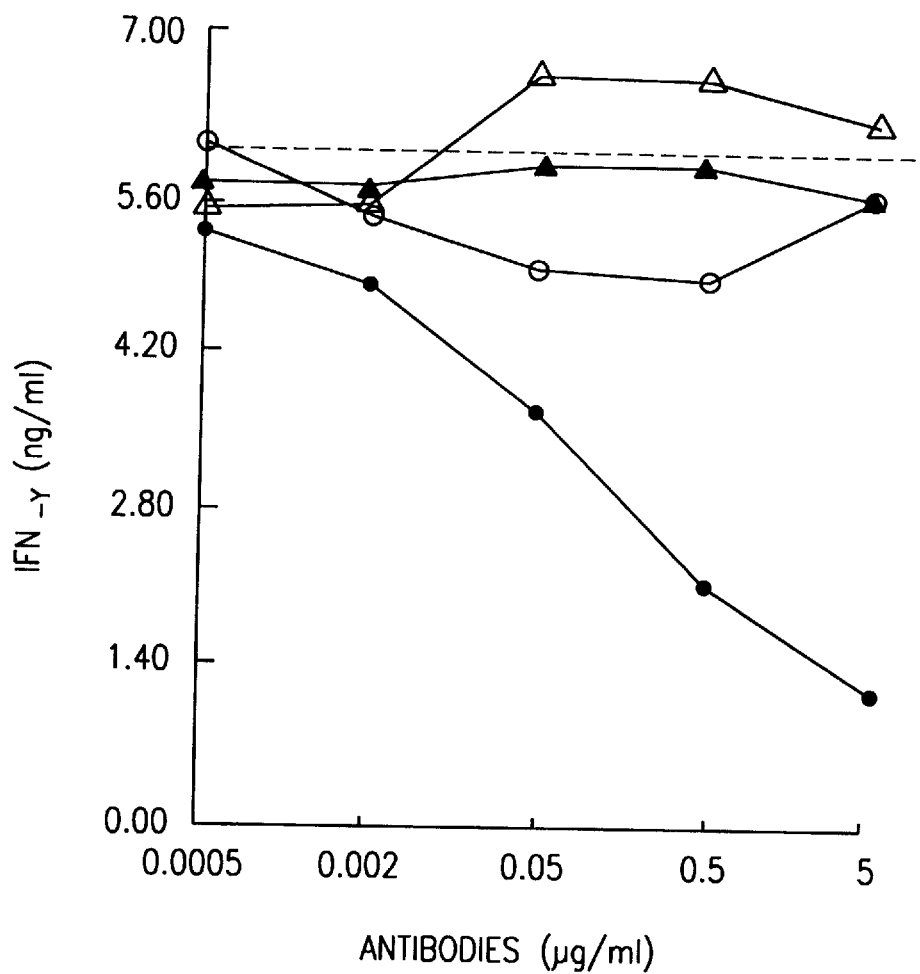

FIG. 22—A Combination of mAbs to IL-12R β Inhibit IL-12-induced IFN-γ Production The production of IFN-γ by human PBMC incubated with IL-12 and IL-2 is inhibited by mAbs to IL-12β chain. Freshly isolated human PBMC were cultured with IL-12 (1 ng/ml) plus. IL-2 (20 units/ml) in the presence or absence of mAbs to IL-12Rβ (2B10 and/or 2*4E6), or rat and mouse isotype control antibodies. After 48 hrs of incubation, the culture supernatants were harvested and tested for IFN-γ by ELISA. The dotted line indicates the amount of IFN-γ produced in control cultures containing IL-12 plus IL-2 without added IgG. No detectable IFN-γ was produced in cultures that did not contain both IL-12 and. IL-2. The data are representative of five experiments with similar results.

DETAILED DESCRIPTION OF THE INVENTION

The present invention relates to a novel monoclonal antibody, 2B10, to the human IL-12 receptor β subunit and a novel combination of monoclonal antibodies to the human IL-12 receptor β subunit, 2B10+2*4E6, which inhibits IL-12 bioactivity. The 2B10 mAb of the invention can be conveniently produced by immunizing host animals with COS-7 cells expressing the IL-12 receptor β subunit as discussed below. Suitable host animals include rodents, such as, for example, mice, rats, rabbits, hamsters and the like, or even possibly higher mammals such as goats, sheep, horses and the like, although the higher mammals are more suitable hosts for preparing polyclonal antibodies. Initial doses and booster shots can be given according to accepted protocols for eliciting immune responses in animals, e.g., in a preferred embodiment rats received an initial dose of about $5 \times 10^7$ transfected COS-7 cells/rat i.p. and three subsequent booster shots of about $5 \times 10^7$ cells over a seven month period. Immunized mice were observed to develop an immune response against the human IL-12R as determined by the ability to bind to BaF3 transfectants that constitutively express IL-12R (FIGS. 13 and 14), which provides a convenient way to screen for hosts which are producing antisera having the desired activity.

B lymphocytes obtained from the spleen, peripheral blood, lymph nodes or other tissue of the host may be used as the monoclonal antibody producing cell for 2B10. Most preferred are B lymphocytes obtained from the spleen. Hybridomas capable of generating the desired monoclonal antibody 2B10 of the invention are obtained by fusing such B lymphocytes with an immortal cell line, that is a cell line which imparts long term tissue culture stability on the hybrid cell. Murine/rat hybridomas which produce the IL-12R monoclonal antibody 2B10 are formed by the fusion of spleen cells from rats immunized against hIL-12R and SP2/0 cells, for example. Chimeric and humanized monoclonal antibodies can be produced by cloning the antibody expressing genes from the hybridoma cells and employing recombinant DNA methods now well known in the art to either join the subsequence of the rat Ig variable region to human constant regions or to combine human framework regions with complementary determining regions (CDR's) from a donor mouse or rat immunoglobulin. (See, for example, EPO Publication No. 0239400). An improved method for carrying out humanization of murine monoclonal antibodies which provides antibodies of enhanced affinities is set forth in International Patent Application No. WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a DNA linker (see Huston et al., Proc. Natl. Acad. Sci. U.S.A., 85, 5879–5883 (1988) and Bird et al., Science, 242, 423–426 (1988).

It is also within the skill of the art to utilize the 2B10 monoclonal antibody and the combination of monoclonal antibodies 2B10 and 2*4E6 of the present invention as therapeutic agents. They may be formulated for parenteral administration in a manner known in the art such as by dissolving the purified monoclonal antibody product either intact or as a fragment in aqueous solutions for injection and sterile filtering. The dosage form may contain known excipients for parenteral administration of proteins such as buffers, stabilizers and carrier protein. The administered dosage will be selected by the attending physician by giving due consideration to the disease severity and nature as well as the age, size and, condition of the patient. As immunoglobulins have demonstrated extended half-lifes in patients, dosing every 10–14 days is usually sufficient. It is also within the skill of the art to modify the monoclonal antibody by forming a hybrid with a toxin molecule such as with a pseudomonas exotoxin or with the A chain of ricin to provide a hybrid molecule capable of destroying the cells expressing the IL-12R in a selective manner.

The invention also pertains to a method for detecting peripheral blood cells which express the IL-12 receptor, which comprises contacting a sample which contains the subject cells with substances capable of forming complexes with the IL-12 receptors so as to form cellular complexes between the substances and the IL-12 receptors, and detecting such cellular complexes. Another embodiment of the invention provides a method of evaluating cell activity in a subject which comprises detecting peripheral blood cells according to the method described above.

In the preferred embodiments, the substances are capable of forming complexes only with the IL-12 receptors present on the surface of peripheral blood cells in which the receptors were expressed. Particularly preferred are substances which comprise anti-IL-12R monoclonal antibody.

The invention also involves a method for diagnosing an immune system abnormality in a subject which comprises determining the number of IL-12R expressing T cells, NK cells, or B-cells in a sample derived from the subject. This method involves contacting the sample with substances capable of forming complexes with the IL-12 receptors and determining the percentage of T cells, NK cells or B cells in the sample which have the IL-12 receptor. Comparing the percentages so determined with the percentage of cells which have the IL-12 receptor in a sample from a normal subject who does not have the immune system abnormality, the differences in the percentage of cells so determined being indicative of the immune system abnormality. Preferably, the subject is an animal, e.g., a human.

As a molecule associated with T cell, NK cell and B cell function, the measurement of IL-12R expression has diagnostic importance. Because high expression of IL-12R is distinctive to activated T cells, NK cells or B cells, it is a marker for these cells in a population of lymphocytes.

Moreover, the level of expression of IL-12R provides a measure of T cell, NK cell or B cell activity. This information may be important for evaluating the immune status of an individual. For instance, in the treating of certain disease, such as cancer, agents which affect the immunocompetency are often used. Assays for IL-12R expression may allow physicians to monitor the immune status of the patient and to adjust treatment to minimize the risk of opportunistic infection, often a threat to immunocompromised patients.

Assays for IL-12R expression may be conventional immunochemical assays for cell surface antigens. Peripheral blood mononuclear cells can be isolated from patient and incubated with IL-12R monoclonal antibody under conditions which allow the antibody to bind the surface antigen. Antibody bound to the cell surface provides, a measure of IL-12R expression. Binding of the antibody to cells may be evaluated by employing an IL-12R monoclonal antibody labeled with a radioactive, fluorescent or other compound capable of being detected.

The invention also involves a method for detecting soluble IL-12 receptor concentration in samples derived from subjects with immune system disorders, cancer, or other diseases that would be marked by an increase or decrease in soluble form of IL-12R. Assays for soluble IL-12R may be conventional sandwich immunochemical assays or $^{125}$I-IL-12 binding assays to immobilized IL-12R.

Information regarding the IL-12R can be found in U.S. patent application Ser. No. 08/094,713, filed Jul. 19, 1993, now abandoned, which is now continuation-in-part application Ser. No. 08/248,532, filed May 31, 1994, now U.S. Pat. No. 5,536,657 the contents of both applications being expressly incorporated by reference herein. See also, Chua, A., et al., *J. Immunol.*, 158:128 (1994).

Information regarding the 2*4E6 mAb can be found in U.S. patent application Ser. No. 08/094,649, filed Jul. 19, 1993, now abandoned, which is now continuation-in-part application Ser. No. 08/248,531, filed May 31, 1994, the contents of both applications being expressly incorporated by reference herein. In addition, FIGS. 1 to 12A–D and the experimental information from these applications are essentaily reproduced as FIGS. 1 to 12A–D and Examples 1 to 16.

Certain embodiments of this invention are exemplified in the Examples which follow. In these sections, possible mechanisms and structures are postulated. The Examples are set forth to aid in an understanding of the invention but are not intended to, and should not be construed to, limit in any way the invention as set forth in the claims which follow.

EXAMPLE 1
Preparation, Characterization & Purification of Hybridoma Antibodies

Balb/c mice (Charles River Laboratories) were immunized by the intraperitoneal route with PHA-activated human PBMC (PHA-activated PBMC) at 6×10$^7$ cells/mouse. Mice received 5 subsequent booster injections of between 2–5×10$^7$ cells over a six month period. For preparation of activated spleen cells, 2 mice were injected intraperitoneally and intravenously with 1×10$^7$ and 2.5×10$^6$ cells, respectively, on two successive days, starting four days prior to the cell fusion. Spleen cells were isolated from these mice and fused with SP2/0 cells at a ratio of 1:1 with 35% v/v polyethylene glycol 4000 (E. Merck) according to the method of Fazekas et al., *J. Immunol. Methods*, 35, 1 (1980). The fused cells were plated at a density of 6×10$^5$ cells/ml/well in 48-well cluster dishes in IMDM supplemented with 10% FBS, glutamine (2 mM), β-mercaptoethanol (0.1 mM), gentamicin (50 g/ml), 5% ORIGEN hybridoma cloning factor (IGEN, Inc.), 5% P388DI supernatant (10) and 100 Units/ml rHuIL-6. Hybridoma supernatants were assayed for specific anti-IL-12 receptor antibodies by: 1) immunoprecipitation of the soluble complex of $^{125}$I-HuIL-12 crosslinked to IL-12 receptor ($^{125}$I-IL-12/IL-12R), 2) inhibition of $^{125}$I-HuIL-12 binding to PHA-activated PBMC'S, and 3) differential binding to IL-12 receptor positive cells versus receptor negative cells. Antibody-producing hybridoma lines were cloned by limiting dilution. Antibodies were purified from ascites fluids by affinity chromatography on Protein G bound to crosslinked agarose according to the manufacturer's protocol (Genex).

EXAMPLE 2
Preparation of Human PHA Lymphoblasts and IL-12 Receptor Binding Assays Human peripheral blood mononuclear cells were isolated (see Gately et al, *J. Natl. Cancer Inst.* 69, 1245 (1982)) and cultured at 37° C. at a density of 5×10$^5$ cells/ml in tissue culture medium (TCM) containing 0.1% PHA-P (Difco). After 3 days, the cultures are split 1:1 with fresh TCM, and human rIL-2 was added to each culture to give a final concentration of 50 units/ml. The cultures were then incubated for an additional 1–2 days, prior to use in assays.

PHA-activated human PBMC were washed once in binding buffer (RPMI-1640, 5% FBS, 25 mM HEPES pH 7.4) and resuspended in binding buffer to a cell density of 7×10$^6$ cells/ml. Lymphoblasts (7×10$^6$ cells) were incubated with various concentrations of $^{125}$I-IL-12 (5–10000 pM) at room temperature for the designated times. Cell bound radioactivity was separated from free $^{125}$I-IL-12 by centrifugation of the assay mixture through 0.1 ml of an oil mixture (1:2 mixture of Thomas Silicone Fluid 6428-R15: A. H. Thomas, and Silicone Oil AR 200: Gallard-Schlessinger) at 4° C. for 90 sec at 10,000×g. The tip containing the cell pellet was excised, and cell bound radioactivity was determined in a gamma counter. Non-specific binding was determined by inclusion of 100 nM unlabeled IL-12 in the assay. Incubations were carried out in duplicate or triplicate. Receptor binding data were analyzed by using the non-linear regression programs EBDA and LIGAND as adapted for the IBM personal computer by McPherson, *J. Pharmacol. Methods*, 14, 213 (1985) from Elsevier-BIOSOFT.

EXAMPLE 3
Affinity Cross-Linking of $^{125}$I-IL-12 to IL-12 Receptor Bearing Cell Lines IL-12 receptor bearing cells were incubated with $^{125}$I-IL-12 (100–500 pM) in the presence or absence of excess unlabeled IL-12 for 2 hr at room temperature. The cells were then washed with ice-cold PBS pH 8.3 (25 mM Sodium Phosphate pH 8.3, 0.15M NaCl and 1 mM MgCl$_2$) and resuspended at a concentration of 0.5–1.0×10$^7$ cells/ml in PBS pH 8.3. BS3 (Pierce) in dimethyl sulfoxide was added to a final concentration of 0.4 mM. Incubation was continued for 30 min. at 4° C. with constant agitation. The cells were washed with ice-cold 25 mM Tris-HCl (pH 7.5), 0.15 mM NaCl and 5 mM EDTA and then solubilized at 0.5–1.0× 10$^8$ cells/ml in solubilization buffer (50 mM Tris-HCl (pH 8.0) containing 8 mM CHAPS, 0.25M NaCl, 5 mM EDTA, 40 µg/ml PMSF, 0.05% NaN3, and 1% BSA) for 1 hr at 4° C. The extracts were centrifuged at 12,000×g for 45 min. at 4° C. to remove nuclei and other debris.

EXAMPLE 4
Immunoprecipitation Assay of the Soluble Complex of $^{125}$I-IL-12 Crosslinked to Human IL-12R For the immunoprecipitation assay, hybridoma culture supernatant (0.5 ml), diluted antisera, or purified IgG was added to a microfuge tube containing 0.1 ml of a 50% suspension of either goat-anti-mouse IgG coupled to agarose (Sigma Chem. Co.) or Protein G coupled to Sepharose 4B (Pharmacia). The assay volume was brought up to 1.0 ml with IP buffer (8 mM CHAPS in PBS (0.25M NaCl), 1% BSA, & 5 mM EDTA) and the mixture was incubated on a rotating mixer for 2 hr at room temperature. The beads were pelleted by centrifugation, resuspended in 1 ml IP buffer containing $^{125}$I-IL-12/IL-12R (10–20,000 cpm) and the mixture was incubated on a rotating mixer for 16 hr at 4° C. After this incubation, the beads were pelleted by centrifugation and washed twice in IP buffer without BSA. The $^{125}$I-labeled receptor complex bound to the solid phase antibodies was released by adding 100 μl of 2× Laemmli sample buffer (Nature, 227, 680 (1970)) with and without 10%-mercaptoethanol and heating for 5 min. at 95° C. The immunoprecipitated proteins were analyzed by SDS-PAGE on 8% or 4–15% gradient polyacrylamide gels and visualized by autoradiography.

EXAMPLE 5
Assays for IL-12R Solubilized from Cells Expressing IL-12 Receptor

To confirm that the antibodies identified by the immunoprecipitation assay were specific for IL-12R, an immunoprecipitation/soluble IL-12R binding assay was developed. As described in Example 1 above, antibodies (as hybridoma supernatant, purified IgG (50 μg) or antisera) were immobilized by binding to goat anti-mouse IgG coupled to agarose (100 μl; Sigma Chemical Co.) or protein G coupled to Sepharose 4B (100 μl; Pharmacia). For some experiments, antibodies were covalently crosslinked to protein G-Sepharose 4B, before being used in the assay (See Stern and Podlaski, Techniques in Protein Chemistry (1993)). The immobilized antibodies were resuspended in IP buffer (0.3 ml) and 0.2 ml of a detergent solubilized extract of PHA-activated PBMCs or K6 cells that contained IL-12R was added. To prepare the detergent solubilized IL-12R preparation, the cells were washed with ice-cold 25 mM Tris-HCl (pH 7.5), 0.15M NaCl and 5 mM EDTA and then solublized at $1.5 \times 10^8$ cells/ml in solubilization buffer (50 mM Tris-HCl, pH 8.0, containing 8 mM CHAPS, 0.25M NaCl, 5 mM EDTA, 40 μg/ml PMSF, 0.05% NaN3, and 1% BSA) for 1 hr at 4° C. The extracts were centrifuged at 120,000×g for 60 min. at 4° C. to remove nuclei and other debris. The mixture was incubated on a rotating mixer for 16 hr at 4° C. After this incubation, the beads were pelleted by centrifugation and resuspended in IP buffer (0.15 ml) containing $^{125}$I-HuIL-12 at concentrations ranging from 0.05 to 7.5 nM. The IL-12R immobilized on the antibody coated beads was incubated with $^{125}$I-HuIL-12 for 2 hrs. at room temperature on a shaker. Following this incubation, the beads were pelleted, washed twice with IP buffer and the bound radioactivity determined in a gamma counter. Non-specific binding was determined by inclusion of 70 nM unlabeled human IL-12 in the assay. Solubilized IL-12R binding data were analyzed according to the method of Scatchard, (Assn. N.Y. Acad. Sci., 51, 660 (1949)) by using the nonlinear regression programs EBDA and Ligand as adapted for the IBM PC by McPherson, from Elsevier-BIOSOFT.

EXAMPLE 6
Competitive Inhibition of $^{125}$I-IL-12 Binding to the IL-12R by Antibodies The ability of hybridoma supernatant solutions, purified IgG, or antisera to inhibit the binding of $^{125}$I-IL-12 to PHA-activated lymphoblasts was measured as follows: serial dilutions of culture supernatants, purified IgG or antisera were mixed with activated lymphoblasts ($1-1.5 \times 10^6$ cells) in binding buffer (RPMI-1640, 5% FBS+25 mM Hepes, pH 7.4) and incubated on an orbital shaker for 1 hour at room temperature. $^{125}$I-HuIL-12 ($1 \times 10^5$ cpm) was added to each tube and incubated for 1–2 hours at room temperature. Non-specific binding was determined by inclusion of 10 nM unlabeled IL-12 in the assay. Incubations were carried out in duplicate or triplicate. Cell bound radioactivity was separated from free $^{125}$I-IL-12 by centrifugation of the assay through 0.1 ml of an oil mixture as described above. The tip containing the cell pellet was excised, and cell bound radioactivity was determined in a gamma counter.

EXAMPLE 7
Labeling of Human IL-12 and Mab 2*4E6 with $^{125}$I

Human IL-12 and purified 2*4E6 IgG were labeled with $^{125}$I by a modification of the Iodogen method (Pierce Chemical Co., Rockford, Ill.). Iodogen was dissolved in chloroform and 0.05 mg dried in a 12× 15 mm borosilicate glass tube. For radiolabeling, 1.0 mCi Na[$^{125}$I] (Amersham, Chicago, Ill.) was added to an Iodogen-coated tube containing 0.05 ml of Tris-iodination buffer (25 mM Tris-HCl pH 7.5, 0.4M NaCl and 1 mM EDTA) and incubated for 4 min at room temperature. The activated $^{125}$I solution was transferred to a tube containing 0.05 to 0.1 ml IL-12 (7 μg) or IgG (100 μg) in Tris-iodination buffer and the reaction was incubated for 9 min at room temperature. At the end of the incubation, 0.05 ml of Iodogen stop buffer (10 mg/ml tyrosine 10% glycerol in Dulbecco's PBS, pH 7.40) was added and reacted for 3 min. The mixture was then diluted with 1.0 ml Tris-iodination buffer, and applied to a Bio-Gel P1ODG desalting column (BioRad Laboratories) for chromatography. The column was eluted with Tris-iodination buffer, and fractions (1 ml) containing the peak amounts of labeled protein were combined and diluted to $1 \times 10^8$ cpm/ml with 1% BSA in Tris-iodination buffer. The TCA preciptable radioactivity (10% TCA final concentration) was typically in excess of 95% of the total radioactivity. The radiospecific activity was typically ~1500 to 2500 cpm/fmol for 2*4E6 IgG and 5000 to 7000 cpm/fmole for IL-12.

EXAMPLE 8
Binding Assays of $^{125}$I-2*4E6 to Intact Cells

PHA-activated human PBMC were washed once in binding buffer (RPMI-1640, 5% FBS and 25 mM Hepes, pH 7.4) and resuspended in binding buffer to a cell density of $1.5 \times 10^7$ cells/ml. Lymphoblasts ($1.5 \times 10^6$ cells) were incubated with various concentrations of $^{125}$I-2*4E6-IgG (0.005 to 2 nM) at room temperature for 1.5 hrs. Cell bound radioactivity was separated from free $^{125}$I-2*4E6 IgG by centrifugation of the assay mixture through 0.1 ml silicone oil at 4° C. for 90 seconds at 10,000×g. The tip containing the cell pellet was excised, and cell bound radioactivity was determined in a gamma counter. Non-specific binding was determined by inclusion of 67 nM unlabeled 2*4E6 IgG in the assay. Incubations were carried out in duplicate or triplicate. Receptor binding data were analyzed by using the nonlinear regression programs EBDA, Ligand and Kinetics as adapted for the IBM personal computer by McPherson, from Elsevier BIOSOFF.

EXAMPLE 9
Expression of Recombinant IL-12R in COS Cells and Determination of $^{125}$I-2*4E6 Binding COS cells ($4-5 \times 10^7$) were transfected by electroporation with 25 μg of plasmid DNA expressing recombinant human IL-12R (Chua, et al., J. Immunol., 153:128 (1994)) in a BioRad Gene Pulser (250 μF, 250 volts) according to the manufacturer's protocol. The cells were plated in a 600 cm$^2$ culture plate, harvested after 72 hours by scraping, washed and resuspended in binding buffer. Transfected cells ($8 \times 10^4$) were incubated with increasing concentrations of $^{125}$I-labeled 2*4E6 or IL-12 at room temperature for 2 hrs. Cell bound radioactivity was separated from free $^{125}$I-labeled 2*4E6 or IL-12 as described above.

EXAMPLE 10
Western Blot Analysis of Soluble IL-12R with mAb 2*4E6

PHA-activated PBMC were washed 3 times with ice-cold PBS and solubilized at 0.5–1×10$^8$ cells/ml in solubilization buffer (50 mM Tris HCl pH 8.0 containing 8 mM CHAPS, 0.25M NaCl, 5 mM EDTA, 40 μg/ml PMSF, 0.05% NaN3 and 1 mg/ml BSA) for 1 hr at 4° C. The extracts were centrifuged at 12,000×g for 45 min. at 4° C. to remove nuclei and other debris. The extracts were incubated with 2*4E6 IgG or control IgG bound to goat-anti-mouse IgG immobilized on cross-linked agarose (Sigma Chemical Co.). The precipitated proteins were released by treatment with 0.1M glycine pH 2.3, neutralized with 3M Tris, mixed with ⅕ volume of 5×Laemmli sample buffer, and separated by SDS/PAGE on 8% pre-cast acrylamide gels (NOVEX). The separated proteins were transferred to nitrocellulose membrane (0.2 gm) for 16 hours at 100 volts in 10 mM Tris-HCl (pH 8.3), 76.8 mM glycine, 20% methanol and 0.01% SDS. The nitrocellulose membrane was blocked with BLOTTO (50% w/v nonfat dry milk in PBS+0.05% Tween 20) and duplicate blots were probed with $^{125}$I-2*4E6 IgG (1×10$^6$ cpm/ml in 8 mM CHAPS in PBS, 0.25M NaCl, 10% BSA and 5 mM EDTA)+unlabelled 2*4E6 IgG (67 nM).

EXAMPLE 11
Analysis of IL-12 Receptor Expression on Human Cells by Fluorescence Activated Cell Sorting with mAb 2*4E6

To stain cells expressing IL-12 receptor, 1×10$^6$ in 100 μl staining buffer (PBS containing 2% FBS and 0.1% NaN3) were incubated with 10 μl of 2*4E6 ascites fluid for 25 min. at 4° C. Cells were then washed twice with staining buffer followed by incubation with a 1:100 dilution of goat F(ab)2 anti mouse Ig-PE (Tago, Burlingame Calif.) for 25 min. at 4° C. The stained cells were washed twice with staining buffer and then analyzed on a FACScan flow cytometer (Becton Dickinson).

Figure 1:
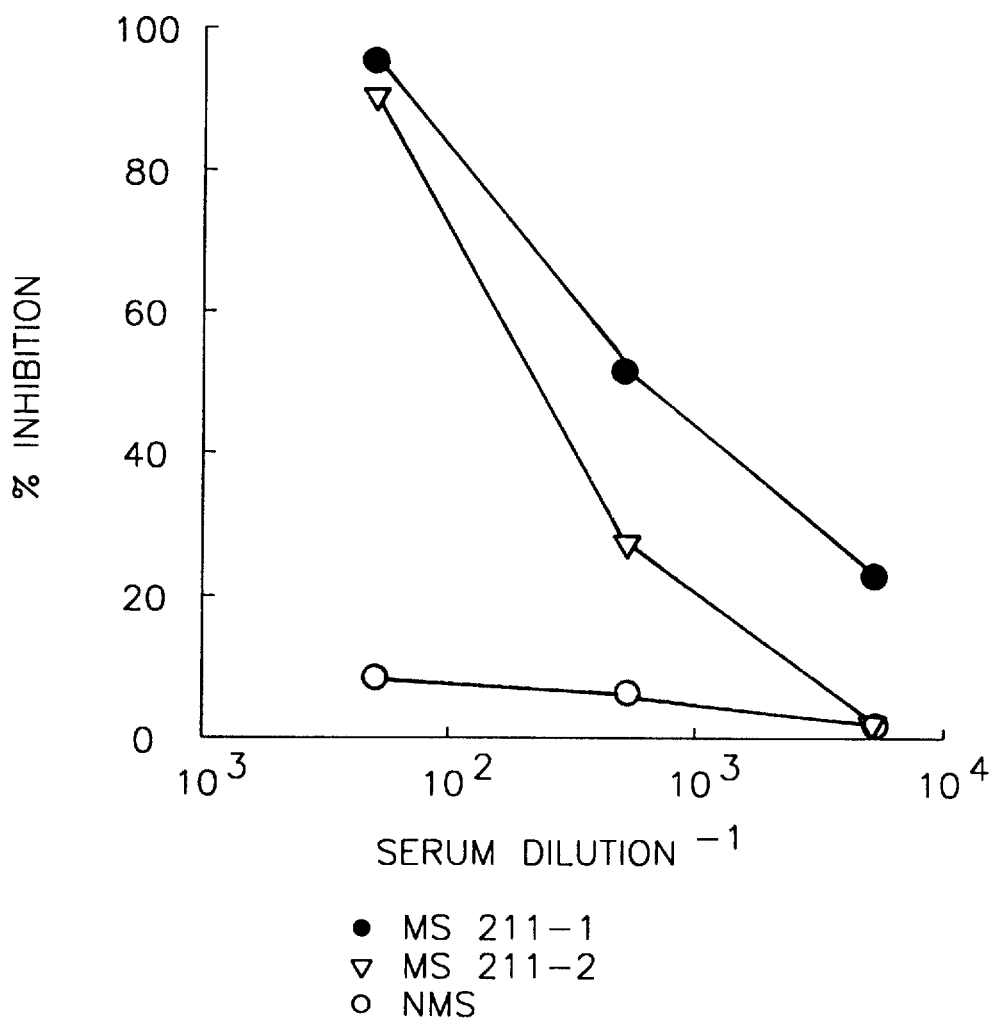
FIG. 1—Inhibition of $^{125}$I-IL-12 Binding to IL-12 Receptor by Mouse Anti-IL-12R Antiserum Ten fold serial dilutions of mouse anti-IL-12R immune serum (#211-1 and #211-2) and normal mouse serum (NMS) were preincubated with PHA-activated PBMC for 60 min at room temperature (RT) before addition of $^{125}$I-IL-12 (100 pM). After addition of $^{125}$I-IL-12, the reaction was incubated for 1–2 hrs at RT and the cell bound radioactivity was determined as discussed below. The data are expressed as the % Inhibition of $^{125}$I-IL-12 binding in the presence of the immune serum when compared to the specific binding in the absence of serum.

EXAMPLE 12
Inhibition of IL-12 Binding to Human PHA-Activated Lymphoblasts by Mouse Anti-IL-12R Antiserum Mice immunized with PHA-activated PBMCs developed an immune response against the human IL-12R as determined by inhibition of $^{125}$I-IL-12 binding to PHA-activated PBMCs (FIG. 1) and immunoprecipitation of the complex of $^{125}$I-IL-12 crosslinked to IL-12R (data not shown). The dilutions for half-maximal inhibition of $^{125}$I-IL-12 binding to PHA-activated PBMCs were ⅟₅₀₀ and ⅟₂₅₀ for animals 211-1 and 211-2, respectively (FIG. 1). These antisera also neutralized IL-12 biologic activity as measured in a PHA-lymphoblast proliferation assay (data not shown). Spleen cells isolated from these mice were fused with SP2/0 myeloma cells and the resulting hybridomas were initially screened for IL-12R specific antibodies by immunoprecipitation of the $^{125}$I-IL-12/IL-12R complex and by inhibition of $^{125}$I-IL-12 binding to IL-12R.

Figure 2:
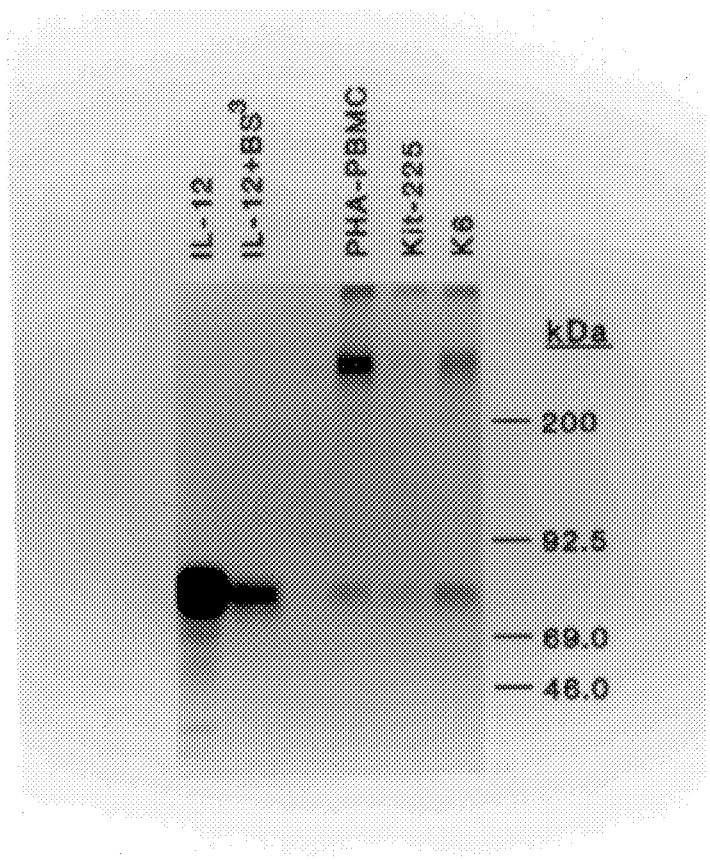
FIG. 2—Characterization of the IL-12 Binding Proteins on IL-12R Positive Human cells by Affinity-Crosslinking PHA-activated PBMC (PHA-PBMC), Kit-225, and Kit-225/K6 (K6) cells (1×10⁷ cells/ml) were incubated with $^{125}$I-IL-12 (100–500 pM) for 2 hrs at room temperature in the absence or presence of 25 nM unlabeled IL-12. Cells were then washed, affinity crosslinked with BS3 (0.4 mM final concentration) and a cell extract prepared as discussed below. The cell extract was precipitated with wheat germ lectin bound to solid supports as discussed below. The precipitated proteins were released by treatment with sample buffer and analyzed by SDS-PAGE and autoradiography on a 8.0% slab gel. The complex of $^{125}$I-IL-12 crosslinked to the IL-12 receptor migrates as a single major band of approximately 210–250 kDa. The band migrating at 75 kDa is $^{125}$I-IL-12 that was bound but not crosslinked to the IL-12 receptor. $^{125}$I-IL-12. (IL-12) and $^{125}$I-IL-12 that was treated with the BS3 crosslinker (IL-12/BS3) were electrophoresed in parallel lanes as markers for the migration of the 75 kDa IL-12 heterodimer and for any oligomers of IL-12 that may form with the BS3 crosslinker. The molecular sizes indicated in the margins were estimated from standards run in parallel lanes. Exposure time was 7 days.
Figure 3:
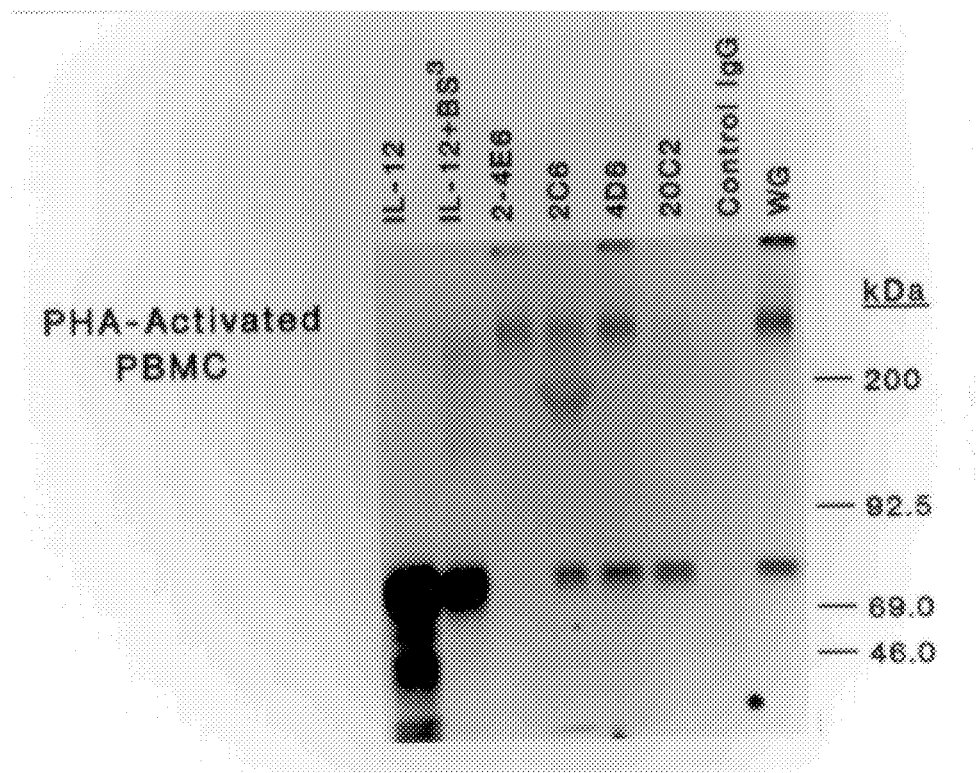
FIG. 3—Immunoprecipitation of the Solubilized $^{125}$I-IL-12/IL-12R Crosslinked Complex by Anti-IL-12R Antibodies Soluble complexes of $^{125}$I-IL-12/IL-12R were prepared from PHA-activiated human PBMC as discussed below and FIG. 2, and immunoprecipitated by immobilized antibodies, 2*4E6, 2C6, 4D6, 20C2 and control. The soluble complexes were also precipitated with wheat germ lectin immobilized on crosslinked agarose (WG) The precipitated proteins were analyzed as discussed below and in FIG. 2. Antibodies 4D6 and 20C2 are non-neutralizing and neutralizing anti-IL-12 antibodies, respectively. 4D6 immunoprecipitates $^{125}$I-IL-12/IL-12R complex and free $^{125}$I-IL-12; whereas 20C2 only immunoprecipitates free $^{125}$I-IL-12. Both 2*4E6 and 2C6 recognize the $^{125}$I-IL-12/IL-12R complex. $^{125}$I-IL-12 (IL-12) and $^{125}$I-IL-12 that was treated with the BS3 crosslinker (IL-12/BS3) were electrophoresed in parallel lanes as markers for the migration of the 75 kDa IL-12 heterodimer and for any oligomers of IL-12 that may form with the BS3 crosslinker. The molecular sizes indicated in the margins were estimated from standards run in parallel lanes. Exposure time was 7 days.
Figure 5B:
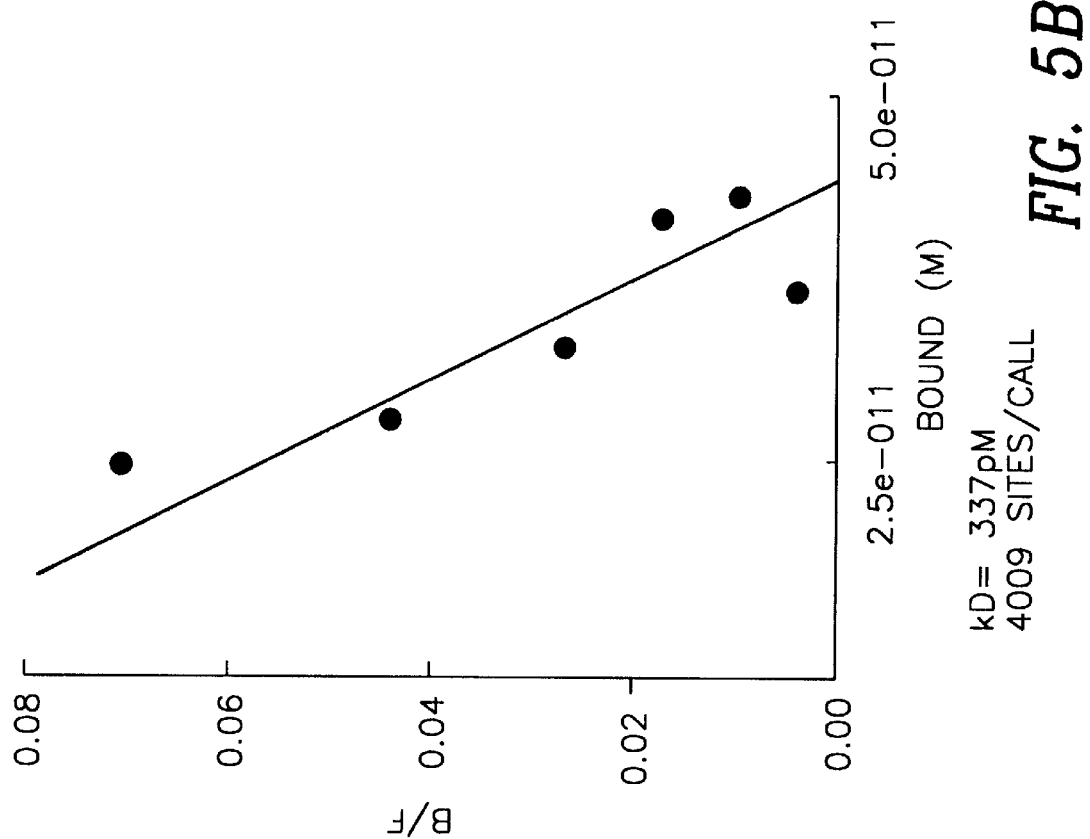
FIGS. 5A and 5B—Equilibrium Binding of $^{125}$I-2*4E6 to Human Kit 225/K6 Cells at Room Temperature
Figure 5A:
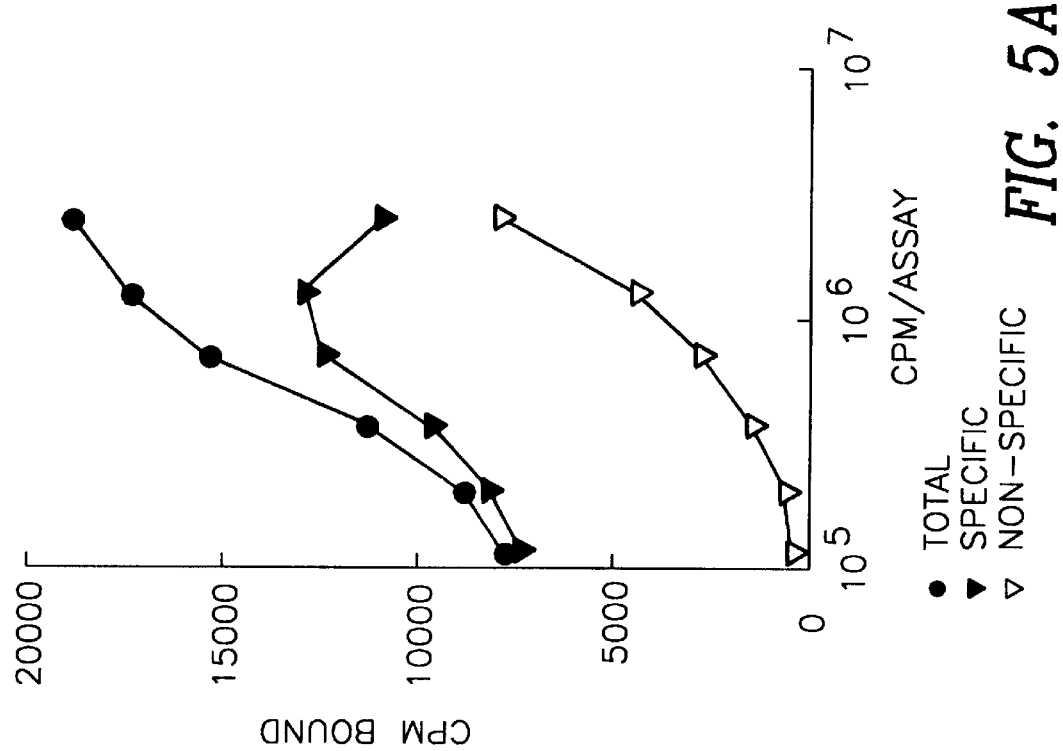

EXAMPLE 13
Identification and Characterization of Monoclonal Anti-IL-12R Antibodies The immunoprecipitation assay identified 13 hybridomas secreting putative non-neutralizing anti-IL-12R antibodies, whereas the IL-12R binding assay identified 3 putative neutralizing IL-12R antibodies (Table 1). The immunoprecipitation assay measured the ability of the putative anti-IL-12R antibodies that are immobilized on a solid phase to capture the solubilized complex of $^{125}$I-IL-12/IL-12R. To verify that the radioactivity immunoprecipitated by the immobilized antibody was present in the complex of $^{125}$I-IL-12/IL-12R, the immunoprecipitated proteins were solubilized, separated by SDS-PAGE and visualized by autoradiography. The preparations of the $^{125}$I-IL-12/IL-12R complexes solubilized from PHA-activated PBMC, Kit-225 and Kit 225/K6. cells were resolved into two major radioactive bands, 210–250 kDa and 75 kDa (FIG. 2). The 210–250 kDa and 75 kDa complexes were identified as the $^{125}$I-IL-12/IL-12R complex and $^{125}$I-IL-12 not complexed with the receptor, respectively (FIG. 2). See also Chizzonite et al., *J. Immunol.*, 148, 3117 (1992). The radioactive 75 kDa band visualized from the cell extracts comigrated with $^{125}$I-IL-12, indicating that it represented $^{125}$I-IL-12 that bound but was not covalently crosslinked to IL-12R. The 210–250 kDa band was not a covalent crosslinked oligomer of $^{125}$I-IL-12 because it was not produced when the crosslinking agent BS3 was added directly to $^{125}$I-IL-12 (FIG. 2).

Hybridoma cells secreting putative anti-IL-12R antibodies were then cloned by limiting dilution and screened by both the immunoprecipitation and inhibition of binding assays that identify non-neutralizing and neutralizing antibodies, respectively. During this cloning and screening process, hybridoma lines secreting putative neutralizing anti-IL-12R antibodies were not recovered, whereas non-meutralizing antibodies were recovered from both the original immunoprecipitation and inhibitory positive hybridomas. After this initial identification and cloning, a direct binding assay was used to determine if the non-neutralizing antibodies only bound to cells expressing IL-12R. This assay demonstrated that the non-neutralizing antibodies could be divided into 2 classes, those that bound only IL-12R postive human cells and those that bound to most human cells (data not shown). Representative antibodies from each class, 2*4E6 and 2C6, respectively, were produced in ascites fluid, purified by protein G affinity chromatography and extensively characterized.

TABLE 1

INITIAL IDENTIFICATION OF HYBRIDOMAS SECRETING ANTI-IL-12 RECEPTOR ANTIBODIES: SPLENOCYTES FROM MICE #211-1 AND #211-2

| | HYBRIDOMA/ANTIBODY | | |
|---|---|---|---|
| | | I.P. ASSAY[1] | |
| | | (cpm bound) | INHIBITION ASSAY[2] |
| | IL-12R 2C6[3] | 1900 | − |
| 211-1 | 1A5 | 722 | − |
| | 4E6 | 840 | − |
| | 5C1 | 312 | + |
| 211-2 | 3B1 | 1323 | − |
| | 4A3 | 2172 | − |
| | 4D6 | 804 | − |
| | 5D5 | 877 | − |
| | 4A5 | 509 | + |
| | 4C6 | 456 | + |
| | 1D1 | 1395 | − |
| | 5E6 | 2043 | − |
| | 2-4E6 | 2836 | − |
| Control mAb | | 402 | |

[1]I.P. assay measures the amount of $^{125}$I-IL-12/IL-12R complex bound by the immobilized antibody.
[2]Inhibition assay measures whether the antibody can inhibit $^{125}$I-IL-12 binding to PHA-activated PBMC.
[3]IL-12R 2C6 is an antibody that both immunoprecipitates the $^{125}$I-IL-12/IL-12R complex and binds to many IL-12R positive and negative human cells. This antibody probably recognizes a component closely associated with the IL-12R.

EXAMPLE 14

Figure 6:
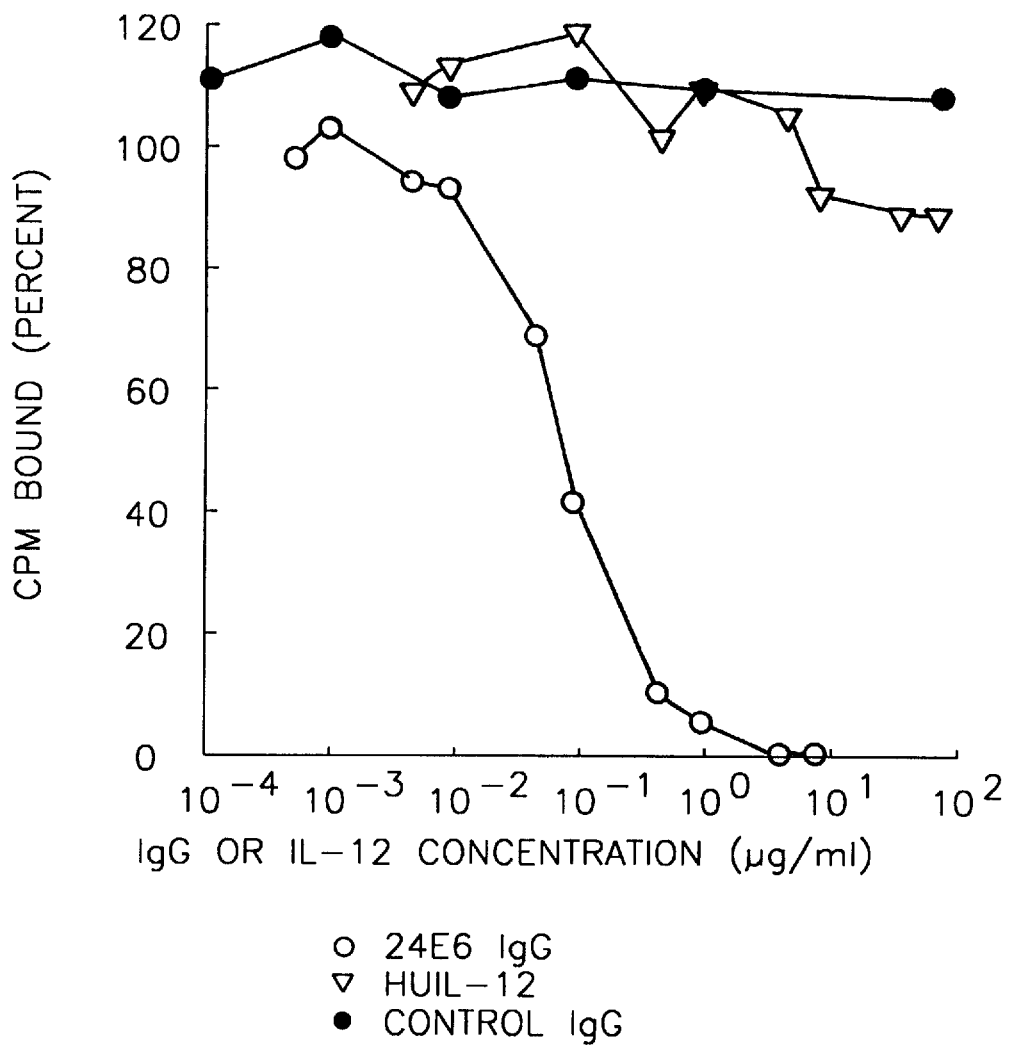
FIG. 6—Inhibition of $^{125}$I-2*4E6 Binding to Kit 225/K6 Cells by Purified 2*4E6 (2*4E6), Human IL-12 (HuIL-12) and Control Antibody (Control IgG)

Characteristics of Monclonal Anti-IL-12R Antibody 2*4E6 Binding to Natural IL-12R MAb 2*4E6 immunoprecipitates the $^{125}$I-IL-12/IL-12R complex solubilized from PHA-activated human lymphoblasts, Kit-225 and Kit 225/K6 cells (FIG. 3, data shown for PHA-activated PBMC), but does not block $^{125}$I-IL-12 binding to IL-12R expressed on these cells. These data suggested that the 2*4E6 antibody was a non-inhibitory or non-neutralizing anti-IL-12R antibody. To confirm that 2*4E6 was a non-inhibitory antibody specific for the IL-12R, 2*4E6 was labelled with $^{125}$I, and direct binding assays were performed with IL-12R positive and negative cells. $^{125}$I-2*4E6 binds to IL-12R-bearing cells with an affinity that ranges from 337 pM to 904 pM and identifies between 1500 and 5000 binding sites per cell (PHA-activated PBMC, FIGS. 4A and 4B; K6 cells, FIG. 5). IL-12 does not block $^{125}$I-2*4E6 from binding to PHA-activated PBMCs and confirms that 2*4E6 is a non-inhibitory/non-neutralizing antibody (FIG. 6). $^{125}$I-2*4E6 binds to other cells expressing IL-12R, such as Kit 225 and YT cells, but does not bind to IL-12R negative cells (non-activated human PBMC, MRC-5 fibroblasts and HL-60 cells) (Table 2).

Equilibrium binding assays have demonstrated that $^{125}$I-IL-12 identifies 3 separate binding sites on the surface of PHA-activated PBMCs, Kit-225 and Kit 225/K6 cells (FIGS. 7A and 7B, data for Kit 225/K6 cells and Table 2). Analysis of this binding data by the method of Scatchard, supra, shows these affinities are approximately 5–20 pM, 50–200 pM and 2–6 nM, respectively. The total number of $^{125}$I-IL-12 binding sites per cell are approximately 1500 to 5000, which is in good agreement with the total number of binding sites identified by $^{125}$I-2*4E6 (Table 2). The data also suggest that 2*4E6 recognizes the low affinity (2–5 nM) binding component of the IL-12 receptor in much the same manner that the anti-TAC antibody recognizes the low affinity component (p55 subunit) of the IL-2 receptor.

Since the data indicated that mAb 2*4E6 was a non-neutralizing antibody specific for the IL-12R, the molecular weight and $^{125}$I-IL-12 binding characteristics of the protein (s) immunoprecipitated by mAb 2*4E6 from the surface of IL-12R postive cells was investigated. The steady state binding of $^{125}$I-IL-12 to proteins immunoprecipitated by immobilized 2*4E6 from solubilized extracts of PHA-activated PBMCs, Kit-225 and Kit 225/K6 cells was saturable and specific (FIGS. 8A and 8B, data for extracts from K6 cells). Transformation of the binding data by the method of Scatchard revealed a single site with an apparent affinity of 188 pM. The proteins immunoprecipitated by 2*4E6 from the cell extracts were resolved by SDS-PAGE, transferred to nitrocellulose membrane and probed with $^{125}$I-2*4E6 in a western blot. On the western blot, $^{125}$I-2*4E6 binds to an approximately 90 kDa protein, that is only immunoprecipitated by 2*4E6 and not by an anti-IL-12 antibody or a control antibody (FIG. 9, data shown for PHA-activated PBMCs). In summary, all the data demonstrated that mAb 2*4E6 bound a protein on the surface of IL-12R positive cells that was approximately 90 kDa and bound $^{125}$I-IL-12 in a specific manner.

TABLE 2

COMPARISON OF THE BINDING OF IL-12 AND 2-4E6 TO HUMAN CELLS EXPRESSING IL-12 RECEPTOR

| | CELL TYPE | | | |
|---|---|---|---|---|
| | IL-12 BINDING[1] | | 2-4E6 BINDING[2] | |
| Human Cells | $K_D$ (nM) | Sites/cell | $K_D$ (nM) | Sites/cell |
| non-activated human PBMC | none detected | | none detected | |
| PHA-PBMC[3] | 0.018 | 312 | 0.745 | 1472–2246 |
| (5–7 days) | 0.084 | 501 | | |
| (3 sites) | 1.800 | 1406 | | |
| K6 cells | 0.016 | 707 | 0.489 | 3116–5259 |
| (3 sites) | 0.057 | 939 | | |
| | 2.400 | 4036 | | |
| Kit-225 | 0.023 | 100 | 0.594 | 1950 |
| (3 sites) | 0.210 | 250 | | |
| | 2.360 | 755 | | |
| YT cells | 0.006 | 24 | 0.904 | 4522 |
| (2 sites) | 0.109 | 117 | | |
| RAJI cells | none detectable | | 0.450 | 561 |
| MRC-5 | none detectable | | none detectable | |
| HL-60 | none detectable | | none detectable | |

[1]Steady state $^{125}$I-IL-12 binding assays. Apparent dissociation constant ($K_D$) and binding sites per cell have been calculated by transformation of the data by the method of Scatchard.
[2]Steady state $^{125}$I-2-4E6 binding assays. Data transformed by the method of Scatchard.
[3]Human peripheral blood mononuclear cells (PBMC) were activated with PHA as described in the methods (PHA-PBMC).

EXAMPLE 15

MAb 2*4E6 Binding To Human Recombinant IL-12R Expressed in COS Cells

The characteristics of the protein bound by mAb 2*4E6 fullfilled standard criterion for an IL-1 2R and therefore 2*4E6 was used in an expression cloning strategy to isolate a cDNA coding for the human IL-12R. A cDNA coding for the human IL-12R β subunit was isolated by this method (Chua, et al., *J. Immunol.*, 153:128 (1994)). The IL-12R β cDNA was engineered into a mammalian cell expression vector, transfected into COS-7 cells and the specificity for binding of $^{125}$I-IL-12 and $^{125}$I-2*4E6 was determined. Steady state binding of $^{125}$I-IL-12 to the rIL-12R-expressing COS cells identifies a single binding site with an apparent affinity of 2–6 nM and approximately 150,000 sites/cell (FIGS. 10A and 10B). This low affinity IL-12 binding site corresponds to the low affinity site seen in the binding assays with human cells that naturally express IL-12R. The binding of $^{125}$I-2*4E6 to rIL-12R β expressed in the COS cells is saturable and specific and identifies approximately 500,000 sites/cell (FIGS. 11A and 11B). COS cells transfected with an unrelated plasmid do not bind either $^{125}$I-IL-12 or $^{125}$I-2*4E6 (data not shown). These data demonstrated unequivocally that mAb 2*4E6 was specific for the low affinity component of the IL-12R.

EXAMPLE 16

Analysis of mAb 2*4E6 Binding to IL-12R Positive Human Cells by Fluorescence Activated Cell Sorting (FACS)

The expression level of IL-12R on human cells could be regulated depending on the activation state of the cells, the cell cycle or the type of environment from which the cells are isolated. Previous data had demonstrated that PHA activation of PBMC leads to a gradual rise in IL-12R expression, reaching a maximum at 3–4 days after activation and declining thereafter. See, Desai et al., *J. Immunol.*, 148, 3125 (1992). To investigate the heterogeneity of IL-12R expression on PHA-activated PBMCs, Kit-225 and Kit 225/K6 cells, FACS analysis of IL-12R on these cells was determined with mAb 2*4E6 (FIGS. 12A, 12B and 12C). The binding of 2*4E6 was specific, and the fluorescence intensity indicated that these three cell types expressed approximately equal numbers of IL-12R. Interestingly, the FACS analysis indicated that the cell population was fairly homogeneous and did not have one population expressing no or low numbers of IL-12R and a second population that expressed very high numbers of IL-12R.

EXAMPLE 17
Production of BaF3 cells expressing IL-12Rβ subunit

BaF3 cells, an IL-3-dependent mouse pro-B cell line (R. Palacios and M. Steinmetz, Cell 41:727 (1985)) were transfected by electroporation with 80 μg of plasmid DNA encoding recombinant human IL-12R β (Chua et al., J. Immunol. 153:128(1994)) in the pRC-RSV expression vector (Invitrogen, San Diego, Calif.), or the pRC-RSV expression vector alone, using a BioRad Gene Pulser (960 μF, 400 volts) according to the manufacturer's protocol. The cells were resuspended in RPMI 1640, 10% FBS, glutamine (2 mM), penicillin G (100 units/ml), streptomycin (100 μg/ml units/ml), and 10% conditioned medium from the WEHI-3 cell line (ATCC, Rockville, Md.; a source of the growth factor IL-3) at a cell density of $2 \times 10^5$ viable cells/ml and incubated at 37° C. under 5% $CO_2$ for 96 hours. Stable transfectants were then selected by their ability to grow in the above growth medium in the presence of 1 mg/ml G-418 (Gibco BRL, Gaithersburg, Md.) by virtue of the neomycin resistance gene present in the pRC-RSV expression vector. Transfectants made with the pRC-RSV vector, expressing only the neomycin resistance gene, were designated BaF3.PRC. Transfectants made with the IL-12R β-containing expression vector were designated BaF3.24E6.

Viable BaF3.24E6 cells were subcloned by limiting dilution in the above growth medium, and subclones were screened for expression of IL-12R β by flow cytometry using anti-IL-12R β monoclonal antibody 2*4E6 as follows. BaF3 transfectant subclones (150 1 μl) were transferred to round bottom 96-well microculture plates, incubated overnight at 37° C., 5% $CO_2$, and then washed two times with PBS, 3% FBS, 0.1% sodium azide (FACS Buffer). The cells were resuspended in 50 μl FACS Buffer, 50 μl of 10 μg/ml 2*4E6 F(ab')$_2$ fragment were added, and the cells were incubated for 60 min at 4° C. with shaking. The cells were washed twice with FACS Buffer, resuspended in 50 μl FACS Buffer, 50 μl of 10 μg/ml affinity purified fluorescein-conjugated goat anti-mouse IgG F(ab')$_2$ fragment (Cappel, Durham, N.C.) were added, and the cells were incubated for 30 min at 4° C. with shaking. The cells were then washed three times with FACS Buffer and analyzed using a Becton-Dickinson FACSort flow cytometer according to the manufacturer's protocols.

EXAMPLE 18
Production, Identification, and Purification of Monoclonal Antibody 2B10

COS-7 cells (ATCC, Rockville, Md.) were transfected by electroporation with 25 μg of plasmid DNA encoding recombinant human IL-12R β in the pEF-BOS expression vector using a BioRad Gene Pulser (250 μF, 350 volts) as described previously (Chua et al., J. Immunol., 153:128 (1994)). Female Lewis rats (Charles River Laboratories) were immunized by the intraperitoneal route with $5 \times 10^7$ IL-12R β transfected COS-7 cells in PBS. The rats received three subsequent booster injections over a seven month period. Three, two, and one day before sacrifice, the rat received injections of $5 \times 10^7$ transfected COS-7 cells. Spleen cells isolated from the rat were fused with SP2/0 cells at a ratio of 1:1 using polyethylene glycol 1500 (Boehringer Mannheim, Germany) as described above. The fused cells were resuspended in IMDM, 10% FBS, glutamine (2 mM), penicillin G (100 units/ml), streptomycin (100 μg/ml), gentamicin (20 μg/ml), β-mercaptoethanol (0.1 mM), 5% conditioned medium from the P388D1 cell line (ATCC, Rockville, Md.), 100 units/ml human IL-6 (Genzyme, Cambridge, Mass.), 5% Hybridoma Cloning Factor (Origen, Rockville, Md.), and 1x HAT (Sigma Chemical Co., St. Louis, Mo.) and plated into 96-well microculture plates at a density of $8 \times 10^4$ total cells/well.

Hybridoma supernatants were assayed for antibodies that bound to BaF3.24E6 cells (subcloned 2F3) but did not bind to BaF3.PRC cells by a modification of the flow cytometry protocol described above using the hybridoma conditioned medium in place of 2*4E6 antibody, and affinity purified fluorescein-conjugated goat anti-rat IgG (Boehringer-Mannheim, Germany). Hybridoma cells secreting putative anti-IL-12R antibodies were subcloned by limiting dilution and rescreened by flow cytometry using BaF3.24E6 and BaF3.PRC cells. Antibodies were purified from ascites fluid by sequential caprylic acid and ammonium sulfate precipitations as previously described (Reik et al., J. Immunol. Methods, 100:123 (1987)).

EXAMPLE 19
Western Blot Analysis Using Horseradish Peroxidase-Conjugated Monoclonal Antibody 2B10

Cell lysates were prepared, SDS polyacrylamide gel electrophoresis was conducted, and electophoretic transfer of proteins to nitrocellulose was performed as described above. Monoclonal antibody 2B10 was conjugated with horseradish peroxidase by a modification of a previously described procedure (Gallati, Clin. Chem. Clin. Biochem., 20:907 (1982); Hakimi et al., J. Immunol., 147:1352 (1991)). Horseradish peroxidase (POD, 0.5 mg; Boehringer-Mannheim, Purity 1) was dissolved in distilled water (0.15 ml), and activated by addition of 0.1M $NaIO_4$ (25 μl) to a final concentration of 14.3 mM for 20 min at room temperature. The reaction was quenched by addition of 0.5M ethylene glycol (25 μl) to a final concentration of 62.5 mM. The activated POD was dialyzed against 5 mM sodium acetate, pH 4.5 for 16 hrs at 4° C. MAb 2B10 (0.5 mg) was dialyzed against 50 mM $NaHCO_3$, pH 8.0, transferred to a glass flask, diluted with 0.4 ml 0.4M $NaHCO_3$, pH 10.5, and reacted with 0.5 mg of activated POD for 2 hrs at room temperature. The reaction was completed by addition of 0.1M $NaBH_4$ (50 μl) for 4–8 hrs at 4° C. The POD-conjugated 2B10 was dialyzed against 0.154M NaCl for 16 hrs at 4° C. and diluted 1:1 with Stock Buffer (0.2M Tris-HCl, pH 7.5, 1% BSA, 0.2% Phenol, and 0.05% Thimerosal). The POD-conjugated 2B10 is stored at 4° C. protected from light. Nitrocellulose membranes were blocked overnight at 4° C. with 5% dry non-fat milk in 50 mM Tris, pH 8.0, 0.01% antifoam A. The membranes were then incubated for 4 hours at 4° C. with 1 μg/ml POD-conjugated 2B10 in PBS containing 0.5M NaCl, 1% BSA, 0.05% Tween 20, and 0.01% Thimerosal, washed five times with 0.2% Tween 20 in PBS, and developed using ECL Western Blotting Detection Reagent (Amersham, Buckinghamshire, England) according to the manufacturer's instructions.

EXAMPLE 20
Measurement of Soluble IL-12R by A Dual Antibody Sandwich ELISA

Immulon II ELISA plates (Dynatech Laboratories Inc., Chantilly, Va.) were coated with mAb by incubation with 2.5 μg/ml 2*4E6 in 50 mM sodium carbonate, pH 9.6 (100 μl/well). The plates were washed with PBS/0.05% Tween 20/0.01% Thimerosal (PBS/Tween), and then incubated with PBS/3% BSA/0.01% Thimerosal (200 μl/well) for 4–5 hr at 37° C. to saturate protein binding sites on the plastic wells. The plates were stored in this blocking solution at 4° C. until use. Before use, plates were washed three times with PBS/Tween, and 50 μl of the test solution was added to the well. The plates were incubated overnight at 4° C., washed three times with PBS/Tween, and 100 μl of 0.142 μg/ml POD-conjugated 2B10, prepared as described above, were added to each well. The plates were incubated at room temperature for 2 hrs, washed four times with PBS/Tween, and 100 μl of peroxidase substrate K-Blue (ELISA Technologies, Lexington, Ky.) were added to each well. Color development was allowed to proceed for 5–15 minutes, and the reaction was stopped by the addition of 100 μl of 1M $H_3PO_4$. The absorbance at 450 nm was measured using a Vmax Microplate Reader (Molecular Devices, Menlo Park, Calif.). The standard consisted of cell lysates of the IL-12R-expressing BaF3.24E6 transfectants ($1 \times 10^8$ cells/ml) prepared as described above. IL-12R Units were calculated assuming 30,000 IL-12R per BaF3.24E6 cell, as determined by Scatchard analysis of $^{125}$I-2*4E6 Fab binding (data not shown).

EXAMPLE 21
Production of Additional Monoclonal Antibodies Against the IL-12R β Subunit Using Transfected COS-7 Cells as Immunogen To facilitate the production and identification of additional mAb against the IL-12R β subunit, we immunized rats with transfected COS-7 cells, prepared as discussed below, which express, on average, $1-3 \times 10^5$ IL-12R β chains/cell. Supernatants from hybridomas produced from the fusion of SP2/0 cells with the splenocytes of these rats were screened by flow cytometry for the ability to bind to BaF3 transfectants that constitutively express IL-12R.

EXAMPLE 22
Analysis of the Expression of the IL-12R β Subunit in BaF3.24E6 Cells The murine pro-B cell line BaF3 was transfected with an expression construct encoding the IL-12R β subunit (yielding BaF3.24E6 cells) or a control expression construct (yielding BaF3.PRC cells), and stable transfectants were isolated as discussed above. A subclone of the BaF3.24E6 cells, clone #2F3, was chosen for use in the hybridoma supernatant screening procedure. FIG. 13 shows that anti-IL-12R β mAb 2*4E6 binds to the BaF3.24E6 cells, but not to the BaF3.PRC cells, demonstrating that the BaF3.24E6 cells express the IL-12R β subunit and could be used as a tool in identifying additional anti-IL-12R β mAb.

EXAMPLE 23
Monoclonal Antibody 2B10 Binding to Recombinant IL-12R β Expressed in BaF3.24E6 Cells Spleen cells isolated from the immunized rats were fused with SP2/0 cells as discussed above and the resulting hybridomas were screened for IL-12R β specific antibodies by flow cytometric analysis of their binding to BaF3.24E6 and BaF3.PRC cells. This assay identified one mAb, designated 2B10, which bound to BaF3.24E6 cells but not to BaF3.PRC cells (FIG. 14), suggesting that mAb 2B10 recognized the IL-12R β subunit.

EXAMPLE 24
Western Blot Analysis of BaF3.24E6 Cell Lysates Using mAb 2B10

To further characterize the antigen recognized by mAb 2B10, cells lysates of BaF3.24E6 and BaF3.PRC cells were analyzed by Western blotting using horseradish peroxidase-conjugated 2B10 as probe. FIG. 15 shows that 2B10 recognizes a group of proteins with molecular weights of ≈95–125 kDa in BaF3.24E6 cells, but not in BaF3.PRC cells. This molecular weight range is consistent with the observed molecular weight of the IL-12Rβ chain in transfected COS-7 cells of 100 kDa (Chua et al., J. Immunol., 153:128 (1994)). The multiple protein bands seen in the BaF3.24E6 cell lysates are probably due to differential glycosylation of the core IL-12R β protein. This data provided further evidence that mAb 2B10 recognized the IL-12R β subunit.

EXAMPLE 25
Immunoprecipitation of the Solubilized $^{125}$I-IL-12/IL-12R Crosslinked Complex from PHA-Activated Lymphoblasts by mAb 2B10

To further demonstrate that mAb 2B10 was directed against the IL-12R, we performed immunoprecipitation studies using $^{125}$I-IL-12/IL-12R crosslinked complexes. Both anti-IL-12R β mAb 2*4E6 and mAb 2B10 specifically immunoprecipitated the same 210–250 kDa protein complex (FIG. 16). In addition, unlike wheat germ lectin, which precipitates free $^{125}$I-IL-12 with a molecular weight of 75 kDa as well as the 210–250 kDa protein band, 2B10 did not precipitate any of the free $^{125}$I-IL-12 present in the crosslinked preparation. These data demonstrate that mAb 2B10 is directed against the IL-12R.

EXAMPLE 26
Inhibition of IL-12 Binding to Transfected COS-7 Cells by Anti-IL-12Rβ Monoclonal Antibodies As discussed above, transfected COS-7 cells expressing the IL-12R β subunit bind $^{125}$I-IL-12 with an apparent affinity of 2–6 nM, which corresponds to the low affinity IL-12 binding site seen with human cells that naturally express IL-12R. In contrast to mAb 2*4E6, mAb 2B10 inhibited binding of $^{125}$I-IL-12 to transfected COS-7 cells expressing the IL-12R β subunit (FIG. 17). A control, isotype-matched rat antibody had no effect on $^{125}$I-IL-12 binding (data not shown). However, to achieve complete inhibition of $^{125}$I-IL-12 binding down to the non-specific binding levels seen when an excess of unlabelled IL-12 is added, a combination of the two mAb 2*4E6 and 2B10 had to be used (FIG. 17). This indicates that whereas mAb 2B10 can inhibit the binding of $^{125}$I-IL-12 to the IL-12R β subunit in COS-7 cells, the combination of 2B10 and 2*4E6 is more effective.

EXAMPLE 27
Inhibition of IL-12 Binding to PHA-Activated Lymphoblasts by Anti-IL-12R β Monoclonal Antibodies Since mAb 2B10 was able to inhibit $^{125}$I-IL-12 binding to the low affinity binding sites expressed on transfected COS-7 cells, the ability of the anti-IL-12R β mAb to inhibit binding of $^{125}$I-IL-12 to the high affinity binding sites present on PHA-activated lymphoblasts was examined. Neither mAb 2*4E6 nor mAb 2B10 inhibited the binding of 50 pM $^{125}$I-IL-12 to PHA-activated lymphoblasts (FIG. 18). However, the combination of the two mAb was able to inhibit up to 90% of the specific binding of $^{125}$I-IL-12 (FIG. 18). These data demonstrate that the combination of the two anti-IL-12R β mAb 2*4E6 and 2B10 is effective at inhibiting $^{125}$I-IL-12 binding to both the low affinity binding site expressed on transfected COS-7 cells and the high affinity binding site naturally expressed on PHA-activated lymphoblasts, suggesting that this combination of mAb, or a bi-specific Ab incorporating the binding specificities of these two mAb, may be useful as an IL-12 antagonist to inhibit the biological activities of IL-12.

EXAMPLE 28

Measurement of Soluble IL-12R β Using A Sandwich ELISA

Soluble forms of many cytokine receptors have been reported. In some cases, the level of soluble cytokine receptor has correlated with patient disease progression. For example, soluble forms of the IL-6R have been detected, and elevated serum levels of soluble IL-6R have been found in HIV seropositive individuals (Honda et al., *J. Immunol.,* 148:2175 (1992)). Soluble forms of the TNFA receptor have been described, and have been shown to be elevated in critically ill endotoxemic patients (Van Zee et al., *Proc. Natl. Acad. Sci. USA,* 89:4845 (1992)). Serum levels of soluble IL-2R have been shown to correlate with immune system activation and disease activity in autoimmune inflammatory disorders and transplantation rejection. Elevated serum levels of soluble IL-2R are a hallmark of a number of hematologic malignancies, including hairy cell leukemia, adult T-cell leukemia, and non-Hodgkin lymphoma (for review, see L. Rubin and D. Nelson, *Annals of Internal Med.,* 113:619 (1990)). In addition, the ability to quantify soluble cytokine receptors may be important when determining the levels of the cytokines themselves in tissue fluids. For example, the ability to quantify IL-1β in synovial fluids was inhibited by the presence of soluble Type II IL-1R (W. Arend et al., *J. Immunol.,* 153:4766 (1994)). Therefore, the ability to measure soluble IL-12R may be an important tool for both diagnostic and therapeutic purposes.

We have developed a dual antibody sandwich enzyme-linked-immunosorbent assay (ELISA) for the measurement of soluble IL-12R β based on the two anti-IL-12R mAb 2*4E6 and 2B10. Soluble IL-12R β is captured onto a 96-well microtitre plate that has been coated with mAb 2*4E6. The captured soluble IL-12R β is detected using horseradish peroxidase-conjugated 2B10, as described herein. A representative standard curve for the soluble IL-12R β ELISA is presented in FIG. 19. Cell lysates of BaF3.PRC transfectants, which do not express IL-12R, were negative in this ELISA (data not shown). The ELISA allows the quantitation of soluble IL-12R β in patient blood and the investigation of the correlation between circulating IL-12R β levels and disease progression.

EXAMPLE 29

IL-12-Induced Proliferation of PHA-activated Human Lymphoblasts

Human peripheral blood mononuclear cells (PBMC) were isolated by centrifugation over discontinuous Ficoll and sucrose gradients as described (Gately et al., *J. Natl. Cancer Inst.,* 69:1245 (1982)). The PBMC ($5\times10^5$ cells/ml) were cultured at 37° C. with 0.1% phytohemagglutinin-P (PHA-P) (Difco Laboratories, Detroit, Mich.) in tissue culture medium (TCM) composed of a 1:1 mixture of RPMI 1640 and Dulbecco's modified Eagle's medium, supplemented with 0.1 mM nonessential amino acids, 60 μg/ml arginine.HCl, 10 mM HEPES buffer, 2 mM L-glutamine, 100 units/ml penicillin, 100 μg/ml streptomycin (all available from GIBCO BRL, Grand Island, N.Y.), $5\times10^{-5}$M 2-mercaptoethanol (Fisher Scientific, Fair Lawn, N.J.), 1 mg/ml dextrose (Fisher), and 5% human AB serum (Irvine Scientific, Santa Ana, Calif.). After 3 days, the cultures were split 1:1 with fresh TCM, and human rIL-2 (provided by Dr. F. Khan, Hoffmann-La Roche Inc.) was added to each culture to give a final concentration of 50 units/ml. The cultures were then incubated for an additional 1 to 2 days, at which time the cells were harvested, washed, and resuspended in TCM at $4\times10^5$ cells/ml. Fifty μl aliquots of the cell suspension were mixed with 25 μl aliquots of various dilutions of anti-IL-12R β mAb 2B10 and/or 2*4E6 in the wells of Costar 3596 flat-bottom microplates. Control cultures received a 1:1 mixture of normal rat IgG and mouse IgG1 (both from Sigma, St. Louis, Mo.) in place of the mAbs. The microplates were incubated for 30 minutes at 37° C., and then 25 μl aliquots of serial dilutions of rHuIL-12, rHuIL-2, rHuIL-7 (Pepro Tech, Inc., Rocky Hill, N.J.), or rHuIL-4 (Genzyme, Cambridge, Mass.) were added to the wells. The cultures were incubated for 42–46 hrs at 37° C. in a humidified atmosphere of 5% $CO_2$ in air, and 50 μl of $^3$H-thymidine (New England Nuclear, Boston, Mass.), 10 μCi/ml in TCM, was then added to each well. The cultures were further incubated 6–7 hrs at 37° C. Subsequently, the culture contents were harvested onto glass fiber filters by means of a cell harvester (Tomtec, Orange, Conn.), and $^3$H-thymidine incorporation into cellular DNA was measured by use of a liquid scintillation counter (Pharmacia LKB Nuclear, Gaithersburg, Md.). All samples were assayed in triplicate.

EXAMPLE 30

LAK Cell Induction and Cytotoxicity Assays

Human PBMC in TCM containing 5% human AB serum were incubated at a final concentration of $2\times10^6$ cells/1-ml culture in 24-well tissue culture plates (Falcon #3047, Becton Dickinson, Lincoln Park, N.J.) in the presence or absence of rHuIL-12. In addition, some cultures received graded concentrations of 2B10 and/or 2*4E6 anti-human IL-12R β mAbs. After incubation for 4 or 5 days at 37° C., the cells were harvested from each culture, washed, resuspended in fresh TCM, and tested for their ability to lyse $^{51}$Cr-labeled Daudi target cells. For labeling, $4\times10^6$ Daudi cells (American Type Culture Collection, Rockville, Md.) were suspended in a solution containing 150 μCi of $^{51}$Cr-sodium chromate (Amersham Corp., Arlington Heights, Ill.) plus 350 μl of LHS medium consisting of Leibovitz's medium (GIBCO BRL), 1% heat-inactivated fetal bovine serum (Hyclone, Logan, Utah), 2 mM L-glutamine, 100 U/ml penicillin, 100 μg/ml streptomycin and 1 mM HEPES buffer (all available from GIBCO BRL). After incubation for 2 hrs in a 37° C. water bath, the $^{51}$Cr-labeled Daudi cells were washed and resuspended at $10^5$ cells/ml in TCM. One hundred μl aliquots of this cell suspension were mixed with equal volumes of cultured PBMC at various effector:target ratios in the wells of Costar 3799 round-bottomed microtiter plates. The plates were centrifuged at 1500 rpm for 5 min, and then incubated for 5 hrs at 37° C. Following this, the plates were again centrifuged at 1500 rpm for 5 min, and the culture supernatants were harvested by use of a Skatron harvesting system (Skatron Instruments Inc., Sterling, Va.) and assayed for radioactivity using a γ-counter (Packard Instrument Co., Downers Grove, Ill.). The percent specific $^{51}$Cr release was calculated as $[(e-c)/(100-c)]\times100$, where e is the percentage of $^{51}$Cr released from target cells incubated with PBMC and c is the percentage of $^{51}$Cr released spontaneously from target cells incubated alone. The total releasable $^{51}$Cr was determined by lysis of the target cells with 2% sodium dodecyl sulfate. All lymphocyte populations were assayed in quadruplicate for lytic activity.

EXAMPLE 31
Induction and Measurement of Human Interferon-γ

For production of interferon-γ (IFN-γ), human PBMC were incubated at a final density of 3×10⁶ cells/ml in TCM containing 5% human AB serum and 20 U/ml rHuIL-2 in the presence or absence of IL-12 with or without 2B10 and/or 2*4E6 anti-IL-12R β mAbs. All cultures were carried out in a total volume of 1 ml in duplicate in Costar 3548 48-well culture plates. After incubation for 48 hr at 37° C., the supernatant fluids were harvested by centrifugation, and assayed in triplicate for IFN-γ use of a specific ELISA performed as follows. ELISA plates (Nunc MaxiSorp, Thousand Oaks, Calif.) were coated overnight at 4° C. with 100 μl of mouse anti-human IFN-γ mAb clone 69 (from Dr. H. Gallati, F. Hoffmann-La Roche Ltd, Basel, Switzerland), 2.5 μg/ml in sodium bicarbonate buffer, pH 9.6. The following day, the contents of the wells were discarded, and the plates were blocked with 200 μl/well 0.5% bovine serum albumin (BSA; Sigma) in phosphate-buffered saline (PBS), pH 7.4, for 1 hr at room temperature.

The plates were then washed 3 times with distilled water, and 100 μl aliquots of serial dilutions of human recombinant IFN-γ (from Dr. H. Gallati) and of experimental samples in PBS with 0.5% BSA plus 0.05% Tween-20 (Sigma) were added to the plates. The plates were subsequently incubated for 2 hrs at room temperature with shaking (500±100 rpm), followed by washing 6 times with distilled water. One hundred μl aliquots of peroxidase-conjugated anti-human IFN-γ mAb clone 69, 300 ng/ml, were added to the wells; and the plates were incubated for an additional 2 hrs at room temperature with shaking. Following washing 6 more times, the plates were developed with 100 μl/well of TMB peroxidase substrate (Kirkegaard & Perry, Gaithersburg, Md.), and the reaction was terminated by adding 50 μl/well of 1M phosphoric acid solution. The absorbance at 450–650 nm was determined with a Vmax Kinetic Microplate Reader (Molecular Devices, Palo Alto, Calif.).

EXAMPLE 32

To assess the role of IL-12R β chain in the proliferative response induced by IL-12, PHA-activated human lymphoblasts were incubated for 48 hrs with human rIL-12, 250 pg/ml, in the presence or absence of anti-IL-12R β chain mAbs, 2B10 and 2*4E6, which are rat and mouse antibodies, respectively, directed against different epitopes of the IL-12R β chain protein. As shown in FIG. 20, 2B10 or 2*4E6 mAbs, when used individually at 0.05–5 μg/ml, had no effects on IL-12-induced lymphoblast proliferation. However, a combination of both mAbs strongly inhibited proliferating a dose-dependent fashion. This inhibitory effect of the anti-IL-12R β mAbs was IL-12-specific, because they did not inhibit lymphoblast proliferation induced by IL-2, IL-7 or IL-4 (FIG. 20, panels B, C, and D, respectively). Addition of the same concentrations of rat IgG plus mouse IgG did not show any effects on proliferative responses induced by any of the 4 cytokines tested. The 2B10 and 2*4E6 mAbs, when used in combination, were also found to inhibit IL-12-induced activation of LAK cell cytolytic activity (FIG. 21). In addition, we evaluated the ability of 2B10 and 2*4E6 mAbs to block IL-12-induced IFN-γ production by freshly isolated human PBMC. PBMC were incubated for 48 hrs in IL-12 (1 ng/ml) and/or IL-2 (20 units/ml). Significant IFN-γ production was observed only in cultures containing both IL-12 and IL-2 (FIG. 22 and data not shown). The induction of IFN-γ by IL-12 plus IL-2 could not be inhibited by either 2B10 or 2*4E6 mAbs used alone. However, 2B10 and 2*4E6 synergized in causing dose-dependent inhibition of IFN-γ production; in contrast, normal rat and mouse IgG had no effect (FIG. 22).

The ability to inhibit IFN-γ production by inhibiting IL-12 with the combination of 2B10 and 2*4E6 mAbs has important ramifications. IL-12 is a key cytokine in the Shwartzman model of endotoxic shock in mice. IL-12, via stimulation of IFN-γ release, has been shown to prime mice for the endotoxin-induced Shwartzman reaction and anti-IL-12 antibodies can prevent lethality this animal model. See, Ozman et al., *J. Exp. Med.*, 180:907 (1994). IFN-γ also contributes to the lethality of endotoxin shock. By inhibiting the bioactivity of IL-12, with combination of mAbs 2B10 and 2*4E6, IFN-γ production is reduced. By reducing IFN-γ production, destructive inflammatory responses during endotoxic shock can be lessened. See, for example, Heinzel, et al., *Infect. Immun.*, 62:4244 (1994).

Additionally, by inhibiting IL-12 activity, paralysis due to experimental allergic encephalomyelitis in mice can be prevented or reduced. Experimental allergic encephalomyelitis is a T cell-mediated autoimmune disease of the central nervous system, which is a mouse model for multiple sclerosis. See, Leonard, et al., *J. Exp. Med.*, 181:381 (1995).

We claim:
1. A combination of human IL-12 receptor specific immunoglobulins which is capable of inhibiting the binding of human IL-12 to the high affinity human IL-12 receptor and is capable of neutralizing human IL-12 bioactivity by binding to the human IL-12 receptor, wherein each individual immunoglobulin is not individually capable of inhibiting the binding of human IL-12 to the high affinity human IL-12 receptor.

* * * * *